(12) United States Patent
Hilpert et al.

(10) Patent No.: US 8,476,264 B2
(45) Date of Patent: Jul. 2, 2013

(54) N-(3-(2-AMINO-6,6-DIFLUORO-4,4A,5,6,7,7A-HEXAHYDRO-CYCLOPENTA[E][1,3]OXAZIN-4-YL)-PHENYLAMIDES AS BACE1 INHIBITORS

(75) Inventors: Hans Hilpert, Muenchenstein (CH); Emmanuel Pinard, Linsdorf (FR); Thomas Woltering, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/609,304

(22) Filed: Sep. 11, 2012

(65) Prior Publication Data
US 2013/0072478 A1    Mar. 21, 2013

(30) Foreign Application Priority Data
Sep. 21, 2011 (EP) .................................. 11182172

(51) Int. Cl.
C07D 265/08 (2006.01)
C07D 413/12 (2006.01)
C07D 417/12 (2006.01)
A61K 31/5355 (2006.01)

(52) U.S. Cl.
USPC ........................................ 514/230.5; 544/90

(58) Field of Classification Search
USPC ........................................ 514/230.5; 544/90
See application file for complete search history.

(56) References Cited

U.S. PATENT DOCUMENTS
3,395,145 A * 7/1968 Hansen et al. .................. 544/71

FOREIGN PATENT DOCUMENTS
WO 2011/069934 6/2011
WO 2011/071135 6/2011

OTHER PUBLICATIONS

Vassar et al., "Science" ((5440)), 286:735-741 (1999).
(International Search Report PCT/E2012/068287 Dec. 3, 2012).
Roberds et al., Hum. Mol. Genet. 10(12):1317-1324 (2001).
Selkoe et al., "Annual Review Cell Biology" 10:373-403 (1994).
McConlogue et al., "J. Biol. Chem." 282(36):26326-26334 (2007).
Luo et al., Nat. Neurosci. 4(3):231-232 (2001).
Hardy et al., "Science" ((5580)), 297:353-356, (2002).

* cited by examiner

Primary Examiner — Kahsay T Habte

(57) ABSTRACT

The present invention provides N-(3-(2-amino-6,6-difluoro-4,4a,5,6,7,7a-hexahydro-cyclopenta[e][1,3]oxazin-4-yl)-phenyl)-amides of formula I

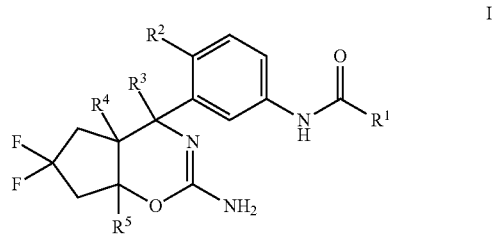

having BACE1 inhibitory activity, their manufacture, pharmaceutical compositions containing them and their use as therapeutically active substances. The active compounds of the present invention are useful in the therapeutic and/or prophylactic treatment of e.g. Alzheimer's disease.

25 Claims, No Drawings

N-(3-(2-AMINO-6,6-DIFLUORO-4,4A,5,6,7,7A-HEXAHYDRO-CYCLOPENTA[E][1,3]OXAZIN-4-YL)-PHENYLAMIDES AS BACE1 INHIBITORS

PRIORITY TO RELATED APPLICATION(S)

This application claims the benefit of European Patent Application No. 11182172.4, filed Sep. 21, 2011, which is hereby incorporated by reference in its entirety.

BACKGROUND OF THE INVENTION

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al., Science. 2002 Jul. 19; 297(5580):353-6; and, Selkoe, Annu Rev Cell Biol. 1994; 10:373-403). Both pathologies are also commonly observed in patients with Down's syndrome (trisomy 21), which also develop AD-like symptoms in early life. Neurofibrillar tangles are intracellular aggregates of the microtubule-associated protein tau (MAPT). Amyloid plaques occur in the extracellular space, their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the trans-membrane domain (TM) to produce a C-terminal fragment of APP containing the TM- and the cytoplasmatic domain (CTFβ). CTFP is the substrate for γ-secretase which cleaves at several adjacent positions within the TM to produce the Aβ peptides and the cytoplasmic fragment. The γ-secretase is a complex of at least 4 different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Science. 1999 Oct. 22; 286(5440):735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Nat Neurosci. 2001 March; 4(3):231-2; and, Roberds et al., Hum Mol Genet. 2001 Jun. 1; 10(12):1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., J Biol Chem. 2007 Sep. 7; 282(36):26326). It is thus presumed that inhibitors of BACE1 activity can be useful agents for therapeutic intervention in Alzheimer's Disease (AD).

The blood-brain barrier is an impediment to the entry of therapeutic substances into the brain. P-glycoprotein (P-gp) is efflux transporters in many tissues including the intestine, brain and kidney. Since P-glycoprotein can actively transport therapeutic substances out of the cell, it is regarded responsible for the penetration of certain therapeutic substances into the brain. The efflux ratio (ER) is a highly sensitive parameter that can be used for the degree of P-gp inhibition.

Furthermore, the formation, or formation and deposition, of β-amyloid peptides in, on or around neurological tissue (e.g., the brain) are inhibited by the present compounds, i.e. inhibition of the Aβ-production from APP or an APP fragment.

SUMMARY OF THE INVENTION

The present invention are novel compounds of formula I, which are N-(3-(2-amino-6,6-difluoro-4,4a,5,6,7,7a-hexahydro-cyclopenta[e][1,3]oxazin-4-yl)-phenyl)-amides. It also provides pharmaceutical compositions containing them, and methods for the production of the compounds and compositions of the invention. Compounds of formula I have BACE1 inhibitory properties, They have improved pharmacological properties such as low ER values. As such, the invention also provides methods for the control or prevention of illnesses such as Alzheimer's disease.

DETAILED DESCRIPTION OF THE INVENTION

The present invention provides compounds of formula I and their pharmaceutically acceptable salts, the preparation of such compounds, pharmaceutical compositions containing them and their manufacture as well as methods for the therapeutic and/or prophylactic treatment of diseases and disorders which are associated with inhibition of BACE1 activity, such as Alzheimer's disease. Furthermore, the formation, or formation and deposition, of β-amyloid plaques in, on or around neurological tissue (e.g., the brain) are inhibited by the present compounds by inhibiting the Aβ production from APP or an APP fragment.

The present invention provides compounds of formula I,

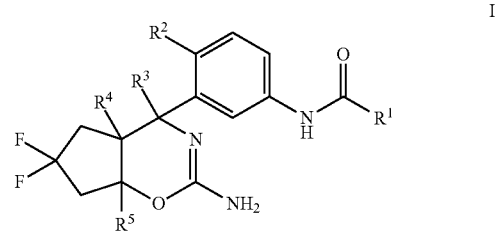

wherein the substituents and variables are as described below and in the claims, or a pharmaceutically acceptable salt thereof.

The present compounds have Asp2 (β-secretase, BACE1 or Memapsin-2) inhibitory activity and therefore can be used in the therapeutic and/or prophylactic treatment of diseases and disorders characterized by elevated β-amyloid levels and/or β-amyloid oligomers and/or β-amyloid plaques and further deposits, particularly Alzheimer's disease.

The following definitions of the general terms used in the present description apply irrespectively of whether the terms in question appear alone or in combination with other groups.

The term "$C_{1-6}$-alkyl", alone or in combination with other groups, stands for a hydrocarbon radical which can be linear or branched, with single or multiple branching, wherein the alkyl group contains 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl, and the like. Particular "$C_{1-6}$-alkyl" groups have 1 to 5 carbon atoms. Specific groups are methyl, ethyl and t-butyl, more specifically methyl.

The term "cyano-$C_{1-6}$-alkyl", alone or in combination with other groups, refers to "$C_{1-6}$-alkyl" as defined herein, which is substituted by one or multiple cyano groups, in particular 1-5 cyano group, more particular 1 cyano group. Examples are cyano-methyl and the like.

The term "halogen-$C_{1-6}$-alkyl", alone or in combination with other groups, refers to "$C_{1-6}$-alkyl" as defined herein, which is substituted by one or multiple halogen atoms, in particular 1-5 halogen atoms, more particularly 1-3 halogen atoms, most particularly 1 halogen atom or 3 halogen atoms. A Particular halogen atom is fluoro. Examples are difluoromethyl, chloromethyl, fluoromethyl and the like. Specific groups are —$CH_2F$ and —$CHF_2$.

The term "$C_{1-6}$-alkoxy-$C_{1-6}$-alkyl", alone or in combination with other groups, refers to "$C_{1-6}$-alkyl" as defined herein, which is substituted by one or multiple "$C_{1-6}$-alkoxy" as defined herein, in particular with 1 "$C_{1-6}$-alkoxy" group. Examples are MeO-Me, 1MeO-Et, 2MeO-Et, 1MeO-2EtO-propyl and the like.

The term "$C_{3-6}$-cycloalkyl-$C_{1-6}$-alkyl", alone or in combination with other groups, refers to "$C_{1-6}$-alkyl" as defined herein, which is substituted by one or multiple "$C_{3-6}$-cycloalkyl" as defined herein, in particular with 1 "$C_{3-6}$-cycloalkyl" group. Examples are cyclopropyl-methyl, cyclohexyl-methyl and the like.

The term "cyano", alone or in combination with other groups, refers to N≡C—.

The term "halogen", alone or in combination with other groups, denotes chloro (Cl), iodo (I), fluoro (F) and bromo (Br). Particular "halogen" atoms are Cl and F. A specific example is F.

The term "aryl", alone or in combination with other groups, refers to an aromatic carbocyclic group containing 6 to 14, in particular 6 to 10, carbon atoms and having at least one aromatic ring or multiple condensed rings in which at least one ring is aromatic. Examples of "aryl" include benzyl, biphenyl, indanyl, naphthyl, phenyl (Ph) and the like. A particular "aryl" group is phenyl.

The term "heteroaryl", alone or in combination with other groups, refers to a cyclic aromatic group having a single 4 to 8 membered ring or multiple condensed rings containing 6 to 14, in particular 6 to 10, ring atoms and containing 1, 2 or 3 heteroatoms individually selected from N, O and S, in particular N and O, in which group at least one heterocyclic ring is aromatic. Examples of "heteroaryl" include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl, pyrrolyl, quinolinyl, tetrazolyl, thiazolyl, thienyl, triazolyl, 6,7-dihydro-5H-[1]pyrindinyl and the like. Particular "heteroaryl" groups are pyridinyl, pyrazinyl, pyrimidinyl, oxazolyl. A specific group is pyridin-2-yl.

The term "$C_{1-6}$-alkoxy", alone or in combination with other groups, stands for an —O—$C_{1-6}$-alkyl radical which is linear or branched, with single or multiple branching, wherein the alkyl group contains 1 to 6 carbon atoms, for example, methoxy (OMe), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" are groups with 1 to 4 carbon atoms. Specific groups are methoxy, ethoxy and ethyoxy.

The term "halogen-$C_{1-6}$-alkoxy", alone or in combination with other groups, refers to "$C_{1-6}$-alkoxy" as defined herein, which is substituted by one or multiple "halogen" as defined herein, in particular fluoro. Particular "halogen-$C_{1-6}$-alkoxy" groups are fluoro-$C_{1-6}$-alkoxy. A specific example is 2,2,2-trifluoro-ethoxy-.

The term "$C_{2-6}$-alkynyl-$C_{1-6}$-alkoxy", alone or in combination with other groups, refers to "$C_{1-6}$-alkoxy" as defined herein, which is substituted by one or multiple "$C_{2-6}$-alkynyl" as defined herein. A particular "$C_{2-6}$-alkynyl-$C_{1-6}$-alkoxy" group is 5-but-2-ynyloxy.

The term "$C_{3-6}$-cycloalkyl-$C_{1-6}$-alkoxy", alone or in combination with other groups, refers to "$C_{1-6}$-alkoxy" as defined herein, which is substituted by one or multiple "$C_{3-6}$-cycloalkyl" as defined herein, in particular with 1 "$C_{3-6}$-cycloalkyl". Examples are cyclopropyl-methoxy (—O—$CH_2$-cyclopropyl), cyclohexyl-methoxy and the like.

The term "$C_{3-6}$-cycloalkyl", alone or in combination with other groups, denotes a monovalent saturated monocyclic or bicyclic hydrocarbon group of 3 to 6 ring carbon atoms, particularly a monovalent saturated monocyclic hydrocarbon group of 3 ring carbon atoms. Bicyclic means consisting of two saturated rings having two carbon atoms in common, i.e. the bridge separating the two rings is either a single bond or a chain of one or two carbon atoms. Particular "$C_{3-6}$-cycloalkyl" groups are monocyclic. Examples for monocyclic groups are cyclopropyl, cyclobutanyl, cyclopentyl, cyclohexyl and cycloheptyl. Examples for bicyclic cycloalkyl are bicyclo[2.2.1]heptanyl, bicyclo[2.2.2]octanyl and adamantanyl. A particular group is cyclopropyl.

The term "$C_{2-6}$-alkynyl", alone or in combination with other groups, denotes a monovalent linear or branched hydrocarbon group of 2 to 6 carbon atoms, in particular from 2 to 4 carbon atoms, and containing one, two or three triple bonds. Examples of "$C_{2-6}$-alkynyl" include ethynyl, propynyl, prop-2-ynyl and n-butynyl. Specific groups are ethynyl and propynyl.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, sulphuric acid, tartaric acid, trifluoroacetic acid and the like. Particular acids are formic acid, trifluoroacetic acid and hydrochloric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. In particular it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values ($-log\ IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values ($-log\ Ki$), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity of the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as in particular, more particular and most particular definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC.

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure.

The invention also provides pharmaceutical compositions, methods of using, and methods of preparing the aforementioned compounds.

All separate embodiments can be combined.

One embodiment of the invention is a compound of formula I,

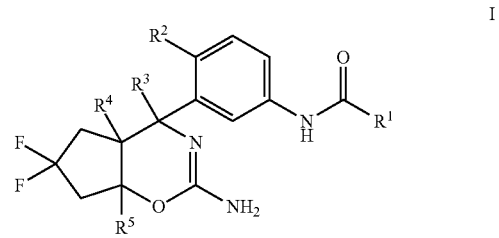

wherein
$R^1$ is selected from the group consisting of
  i) aryl,
  ii) aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl,
  iii) heteroaryl, and
  iv) heteroaryl substituted by 1-4 substituents individually selected from $C_{3-6}$-cycloalkyl-$C_{1-6}$-alkoxy, $C_{3-6}$-cycloalkyl-$C_{1-6}$-alkyl, cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl;
$R^2$ is selected from the group consisting of
  i) hydrogen,
  ii) $C_{1-6}$-alkyl, and
  iii) halogen;
$R^3$ is selected from the group consisting of
  i) $C_{1-6}$-alkyl and
  ii) halogen-$C_{1-6}$-alkyl;
$R^4$ is selected from the group consisting of
  i) hydrogen and
  ii) $C_{1-6}$-alkyl; and
$R^5$ is selected from the group consisting of
  i) hydrogen,
  ii) $C_{1-6}$-alkyl, and
  iii) halogen-$C_{1-6}$-alkyl;
or pharmaceutically acceptable salts thereof.

A certain embodiment of the invention provides a compound of formula I, wherein $R^1$ is heteroaryl substituted by 1-2 substituents individually selected from $C_{3-6}$-cycloalkyl-$C_{1-6}$-alkoxy, cyano, halogen, halogen-$C_{1-6}$-alkoxy, halogen-$C_{1-6}$-alkyl, $C_{1-6}$-alkoxy, $C_{2-6}$-alkynyl-$C_{1-6}$-alkoxy and $C_{1-6}$-alkyl;
$R^2$ is halogen;
$R^3$ is selected from the group consisting of
  i) $C_{1-6}$-alkyl and
  ii) halogen-$C_{1-6}$-alkyl;
$R^4$ is hydrogen;

$R^5$ is selected from the group consisting of
  i) hydrogen and
  ii) halogen-$C_{1-6}$-alkyl;
or pharmaceutically acceptable salts thereof.

A certain embodiment of the invention provides a compound of formula I, wherein
$R^1$ is selected from the group consisting of
  i) aryl,
  ii) aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl,
  iii) heteroaryl, and
  iv) heteroaryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl;
$R^2$ is selected from the group consisting of
  i) hydrogen,
  ii) $C_{1-6}$-alkyl, and
  iii) halogen;
$R^3$ is selected from the group consisting of
  i) $C_{1-6}$-alkyl and
  ii) halogen-$C_{1-6}$-alkyl;
$R^4$ is selected from the group consisting of
  i) hydrogen and
  ii) $C_{1-6}$-alkyl; and
$R^5$ is selected from the group consisting of
  i) hydrogen and
  ii) $C_{1-6}$-alkyl;
or pharmaceutically acceptable salts thereof.

A certain embodiment of the invention provides a compound of formula I, which is of formula Ia.

A certain embodiment of the invention provides a compound of formula I as described herein, wherein $R^1$ is heteroaryl.

A certain embodiment of the invention provides a compound of formula I as described herein, wherein $R^1$ is aryl.

A certain embodiment of the invention provides a compound of formula I as described herein, wherein $R^1$ is aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl.

A certain embodiment of the invention provides a compound of formula I as described herein, wherein $R^1$ is heteroaryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl.

A certain embodiment of the invention provides a compound of formula I as described herein, wherein $R^1$ is heteroaryl substituted by 1-2 substituents individually selected from $C_{3-6}$-cycloalkyl-$C_{1-6}$-alkoxy, cyano, halogen, halogen-$C_{1-6}$-alkoxy, halogen-$C_{1-6}$-alkyl, $C_{1-6}$-alkoxy, $C_{2-6}$-alkynyl-$C_{1-6}$-alkoxy and $C_{1-6}$-alkyl.

A certain embodiment of the invention provides a compound of formula I as described herein, wherein $R^1$ is pyridinyl, pyrazinyl, pyrimidinyl, oxazolyl or 1H-pyrazolyl, each substituted by 1-2 substituents individually selected from $C_{3-6}$-cycloalkyl-$C_{1-6}$-alkoxy, cyano, halogen, halogen-$C_{1-6}$-alkoxy, halogen-$C_{1-6}$-alkyl, $C_{1-6}$-alkoxy, $C_{2-6}$-alkynyl-$C_{1-6}$-alkoxy and $C_{1-6}$-alkyl.

A certain embodiment of the invention provides a compound of formula I as described herein, wherein $R^1$ is heteroaryl substituted by 1-2 substituents individually selected from cyano, halogen, halogen-$C_{1-6}$-alkoxy and $C_{2-6}$-alkynyl-$C_{1-6}$-alkoxy.

A certain embodiment of the invention provides a compound of formula I as described herein, wherein $R^1$ is 5-difluoromethoxy-pyrazin-2-yl, 5-difluoromethyl-pyrazin-2-yl, 5-cyclopropylmethoxy-pyrazin-2-yl, 5-fluoromethoxy-pyrazin-2-yl, 5-chloro-pyrazin-2-yl, 5-trifluoromethyl-pyrazin-2-yl, 5-methoxy-pyrazin-2-yl, 5-fluoromethoxy-pyrazin-2-yl, 5-chloro-pyrazin-2-yl, 5-difluoromethyl-pyrazin-2-yl, 5-difluoromethoxy-pyrazin-2-yl, 5-methoxy-pyrazin-2-yl, 5-(2,2,2-trifluoro-ethoxy)-pyrazin-2-yl, 5-(1,1-difluoro-ethyl)-pyrazin-2-yl, 5-(2,2-difluoro-ethoxy)-pyrazin-2-yl, 3,5-dichloro-pyridin-2-yl, 3,5-difluoro-pyridin-2-yl, 3-chloro-5-cyano-pyridin-2-yl, 3-chloro-5-trifluoromethyl-pyridin-2-yl, 3-fluoro-5-trifluoromethyl-pyridin-2-yl, 3-fluoro-pyridin-2-yl, 5-(2,2,2-trifluoro-ethoxy)-pyridin-2-yl, 5-(2,2,3,3,3-pentafluoro-propoxy)-pyridin-2-yl, 5-(2,2,3,3-Tetrafluoro-propoxy)-pyridine-2-yl, 5-(2,2-difluoro-ethoxy)-pyridin-2-yl, 5-but-2-ynyloxy-pyridin-2-yl, 5-chloro-pyridin-2-yl, 5-cyano-3-fluoro-pyridin-2-yl, 5-cyano-pyridin-2-yl, 5-cyclopropylmethoxy-pyridine-2-yl, 5-difluoromethoxy-pyridin-2-yl, 5-fluoro-pyridine-2-yl, 5-trifluoromethyl-pyridin-2-yl1-methyl-1H-pyrazol-3-yl, 4-chloro-1-difluoromethyl-1H-pyrazol-3-yl, -trifluoromethyl-pyrimidin-2-yl or 5-chloro-pyrimidin-2-yl.

A certain embodiment of the invention provides a compound of formula I as described herein, wherein $R^1$ is pyridinyl substituted by 1-2 substituents individually selected from cyano, halogen, halogen-$C_{1-6}$-alkoxy and $C_{2-6}$-alkynyl-$C_{1-6}$-alkoxy.

A certain embodiment of the invention provides a compound of formula I as described herein, wherein $R^1$ is pyridinyl substituted by 1-2 substituents individually selected from $C_{3-6}$-cycloalkyl-$C_{1-6}$-alkoxy, halogen-$C_{1-6}$-alkyl, cyano, halogen, halogen-$C_{1-6}$-alkoxy and $C_{2-6}$-alkynyl-$C_{1-6}$-alkoxy.

A certain embodiment of the invention provides a compound of formula I as described herein, wherein $R^1$ is 3,5-dichloro-pyridin-2-yl, 3,5-difluoro-pyridin-2-yl, 3-chloro-5-cyano-pyridin-2-yl, 3-chloro-5-trifluoromethyl-pyridin-2-yl, 3-fluoro-5-trifluoromethyl-pyridin-2-yl, 3-fluoro-pyridin-2-yl, 5-(2,2,2-trifluoro-ethoxy)-pyridin-2-yl, 5-(2,2,3,3,3-pentafluoro-propoxy)-pyridin-2-yl, 5-(2,2,3,3-Tetrafluoro-propoxy)-pyridine-2-yl, 5-(2,2-difluoro-ethoxy)-pyridin-2-yl, 5-but-2-ynyloxy-pyridin-2-yl, 5-chloro-pyridin-2-yl, 5-cyano-3-fluoro-pyridin-2-yl, 5-cyano-pyridin-2-yl, 5-cyclopropylmethoxy-pyridine-2-yl, 5-difluoromethoxy-pyridin-2-yl, 5-fluoro-pyridine-2-yl or 5-trifluoromethyl-pyridin-2-yl.

A certain embodiment of the invention provides a compound of formula I as described herein, wherein $R^1$ is 5-chloro-pyridine-2-yl, 5-cyano-pyridine-2-yl, 5-fluoro-pyridine-2-yl, 3,5-dichloro-pyridine-2-yl or 5-but-2-ynyloxy-pyridine-2-yl.

A certain embodiment of the invention provides a compound of formula I as described herein, wherein $R^1$ is 5-chloro-pyridine-2-yl.

A certain embodiment of the invention provides a compound of formula I as described herein, wherein $R^1$ is 5-cyano-pyridine-2-yl.

A certain embodiment of the invention provides a compound of formula I as described herein, wherein $R^1$ is 5-fluoro-pyridine-2-yl.

A certain embodiment of the invention provides a compound of formula I as described herein, wherein $R^1$ is 3,5-dichloro-pyridine-2-yl.

A certain embodiment of the invention provides a compound of formula I as described herein, wherein $R^1$ is 5-but-2-ynyloxy-pyridine-2-yl.

A certain embodiment of the invention provides a compound of formula I as described herein, wherein $R^1$ is 3,5-difluoro-pyridin-2-yl.

A certain embodiment of the invention provides a compound of formula I as described herein, wherein $R^1$ is 3-chloro-5-cyano-pyridin-2-yl.

A certain embodiment of the invention provides a compound of formula I as described herein, wherein $R^1$ is 3-chloro-5-trifluoromethyl-pyridin-2-yl.

A certain embodiment of the invention provides a compound of formula I as described herein, wherein $R^1$ is 3-fluoro-5-trifluoromethyl-pyridin-2-yl.

A certain embodiment of the invention provides a compound of formula I as described herein, wherein $R^1$ is 3-fluoro-pyridin-2-yl.

A certain embodiment of the invention provides a compound of formula I as described herein, wherein $R^1$ is 5-(2,2,2-trifluoro-ethoxy)-pyridin-2-yl.

A certain embodiment of the invention provides a compound of formula I as described herein, wherein $R^1$ is 5-(2,2,3,3,3-pentafluoro-propoxy)-pyridin-2-yl.

A certain embodiment of the invention provides a compound of formula I as described herein, wherein $R^1$ is 5-(2,2,3,3-Tetrafluoro-propoxy)-pyridine-2-yl.

A certain embodiment of the invention provides a compound of formula I as described herein, wherein $R^1$ is 5-(2,2-difluoro-ethoxy)-pyridin-2-yl.

A certain embodiment of the invention provides a compound of formula I as described herein, wherein $R^1$ is 5-cyano-3-fluoro-pyridin-2-yl.

A certain embodiment of the invention provides a compound of formula I as described herein, wherein $R^1$ is 5-cyclopropylmethoxy-pyridine-2-yl.

A certain embodiment of the invention provides a compound of formula I as described herein, wherein $R^1$ is 5-difluoromethoxy-pyridin-2-yl.

A certain embodiment of the invention provides a compound of formula I as described herein, wherein $R^1$ is 5-trifluoromethyl-pyridin-2-yl.

A certain embodiment of the invention provides a compound of formula I as described herein, wherein $R^1$ isoxazolyl substituted by 1-2 $C_{1-6}$-alkyl.

A certain embodiment of the invention provides a compound of formula I as described herein, wherein $R^1$ is 2-methyl-oxazol-4-yl.

A certain embodiment of the invention provides a compound of formula I as described herein, wherein $R^1$ is pyrazinyl substituted by 1-2 substituents individually selected from halogen, $C_{1-6}$-alkoxy, $C_{3-6}$-cycloalkyl-$C_{1-6}$-alkoxy, halogen-$C_{1-6}$-alkoxy and halogen-$C_{1-6}$-alkyl.

A certain embodiment of the invention provides a compound of formula I as described herein, wherein $R^1$ is 5-difluoromethoxy-pyrazin-2-yl, 5-difluoromethyl-pyrazin-2-yl, 5-cyclopropylmethoxy-pyrazin-2-yl, 5-fluoromethoxy-pyrazin-2-yl, 5-chloro-pyrazin-2-yl, 5-trifluoromethyl-pyrazin-2-yl, 5-methoxy-pyrazin-2-yl, 5-fluoromethoxy-pyrazin-2-yl, 5-chloro-pyrazin-2-yl, 5-difluoromethyl-pyrazin-2-yl, 5-difluoromethoxy-pyrazin-2-yl, 5-methoxy-pyrazin-2-yl, 5-(2,2,2-trifluoro-ethoxy)-pyrazin-2-yl, 5-(1,1-difluoro-ethyl)-pyrazin-2-yl or 5-(2,2-difluoro-ethoxy)-pyrazin-2-yl.

A certain embodiment of the invention provides a compound of formula I as described herein, wherein $R^1$ is 5-difluoromethoxy-pyrazin-2-yl.

A certain embodiment of the invention provides a compound of formula I as described herein, wherein $R^1$ is 5-difluoromethyl-pyrazin-2-yl.

A certain embodiment of the invention provides a compound of formula I as described herein, wherein $R^1$ is 5-cyclopropylmethoxy-pyrazin-2-yl.

A certain embodiment of the invention provides a compound of formula I as described herein, wherein $R^1$ is 5-fluoromethoxy-pyrazin-2-yl.

A certain embodiment of the invention provides a compound of formula I as described herein, wherein $R^1$ is 5-chloro-pyrazin-2-yl.

A certain embodiment of the invention provides a compound of formula I as described herein, wherein $R^1$ is 5-trifluoromethyl-pyrazin-2-yl.

A certain embodiment of the invention provides a compound of formula I as described herein, wherein $R^1$ is 5-methoxy-pyrazin-2-yl.

A certain embodiment of the invention provides a compound of formula I as described herein, wherein $R^1$ is 5-fluoromethoxy-pyrazin-2-yl.

A certain embodiment of the invention provides a compound of formula I as described herein, wherein $R^1$ is 5-chloro-pyrazin-2-yl.

A certain embodiment of the invention provides a compound of formula I as described herein, wherein $R^1$ is 5-difluoromethyl-pyrazin-2-yl.

A certain embodiment of the invention provides a compound of formula I as described herein, wherein $R^1$ is 5-difluoromethoxy-pyrazin-2-yl.

A certain embodiment of the invention provides a compound of formula I as described herein, wherein $R^1$ is 5-methoxy-pyrazin-2-yl.

A certain embodiment of the invention provides a compound of formula I as described herein, wherein $R^1$ is 5-(2,2,2-trifluoro-ethoxy)-pyrazin-2-yl.

A certain embodiment of the invention provides a compound of formula I as described herein, wherein $R^1$ is 5-(1,1-difluoro-ethyl)-pyrazin-2-yl.

A certain embodiment of the invention provides a compound of formula I as described herein, wherein $R^1$ is 5-(2,2-difluoro-ethoxy)-pyrazin-2-yl.

A certain embodiment of the invention provides a compound of formula I as described herein, wherein $R^1$ is 1H-pyrazolyl substituted by 1-2 substituents individually selected from halogen, halogen-$C_{1-6}$-alkyl and $C_{1-6}$-alkyl.

A certain embodiment of the invention provides a compound of formula I as described herein, wherein $R^1$ is 1-methyl-1H-pyrazol-3-yl or 4-chloro-1-difluoromethyl-1H-pyrazol-3-yl.

A certain embodiment of the invention provides a compound of formula I as described herein, wherein $R^1$ is 1-methyl-1H-pyrazol-3-yl.

A certain embodiment of the invention provides a compound of formula I as described herein, wherein $R^1$ is 4-chloro-1-difluoromethyl-1H-pyrazol-3-yl.

A certain embodiment of the invention provides a compound of formula I as described herein, wherein $R^1$ is pyrimidinyl substituted by 1-2 substituents individually selected from halogen and halogen-$C_{1-6}$-alkyl.

A certain embodiment of the invention provides a compound of formula I as described herein, wherein $R^1$ is 5-trifluoromethyl-pyrimidin-2-yl or 5-chloro-pyrimidin-2-yl.

A certain embodiment of the invention provides a compound of formula I as described herein, wherein $R^1$ is 5-trifluoromethyl-pyrimidin-2-yl.

A certain embodiment of the invention provides a compound of formula I as described herein, wherein $R^1$ is -chloro-pyrimidin-2-yl.

A certain embodiment of the invention provides a compound of formula I as described herein, wherein $R^2$ is halogen.

A certain embodiment of the invention provides a compound of formula I as described herein, wherein $R^2$ is F.

A certain embodiment of the invention provides a compound of formula I as described herein, wherein $R^3$ is methyl, —$CHF_2$ or —$CH_2F$.

A certain embodiment of the invention provides a compound of formula I as described herein, wherein $R^3$ is methyl.

A certain embodiment of the invention provides a compound of formula I as described herein, wherein $R^3$ is —$CH_2F$.

A certain embodiment of the invention provides a compound of formula I as described herein, wherein $R^3$ is methyl, —$CHF_2$.

A certain embodiment of the invention provides a compound of formula I as described herein, wherein $R^4$ is hydrogen.

A certain embodiment of the invention provides a compound of formula I as described herein, wherein $R^5$ is hydrogen.

A certain embodiment of the invention provides a compound of formula I as described herein, wherein $R^4$ is methyl.

A certain embodiment of the invention provides a compound of formula I as described herein, wherein $R^5$ is methyl.

A certain embodiment of the invention provides a compound of formula I as described herein, wherein $R^5$ is hydrogen or —$CH_2F$.

A certain embodiment of the invention provides a compound of formula I as described herein, wherein $R^5$ is —$CH_2F$.

A certain embodiment of the invention provides a compound of formula I as described herein, selected from the group consisting of 5-But-2-ynyloxy-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Cyclopropylmethoxy-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Difluoromethoxy-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Trifluoromethyl-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 3-Chloro-5-trifluoromethyl-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 3-Fluoro-5-trifluoromethyl-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 3-Chloro-5-cyano-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Cyano-3-fluoro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Difluoromethoxy-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Difluoromethyl-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Cyclopropylmethoxy-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Fluoromethoxy-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Trifluoromethyl-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Trifluoromethyl-pyrimidine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 1-Methyl-1H-pyrazole-3-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 4-Chloro-1-difluoromethyl-1H-pyrazole-3-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Cyano-pyridine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide, 5-Chloro-pyridine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide, 5-Fluoromethoxy-pyrazine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide, 5-Chloro-pyrazine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide, 5-Difluoromethyl-pyrazine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide, 5-Difluoromethoxy-pyrazine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide, 5-Methoxy-pyrazine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide, 4-Chloro-1-difluoromethyl-1H-pyrazole-3-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide, 2-Methyl-oxazole-4-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide, 5-(2,2,2-Trifluoro-ethoxy)-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-(2,2,2-Trifluoro-ethoxy)-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-(2,2,3,3-Tetrafluoro-propoxy)-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-(2,2,3,3,3-Pentafluoro-propoxy)-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Chloro-pyridine-2-carboxylic acid [3-((4S,4aR,7aR)-2-amino-6,6-difluoro-4-methyl-4,4a,5,6,7,7a-hexahydro-cyclopenta[e][1,3]oxazin-4-yl)-4-fluoro-phenyl]-amide, 5-Cyano-pyridine-2-carboxylic acid [3-((4S,4aR,7aR)-2-amino-6,6-difluoro-4-methyl 4,4a,5,6,7,7a-hexahydro-cyclopenta[e][1,3]oxazin-4-yl)-4-fluoro-phenyl]-amide, 5-Cyano-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Chloro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Fluoro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 3-Fluoro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Chloro-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Methoxy-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Chloro-pyrimidine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 2-Methyl-oxazole-4-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Cyano-pyridine-2-carboxylic acid [3-((1S,7aS)-2-(R)-amino-6,6-difluoro-4,7a-bis-fluoromethyl-4,4a,5,6,7,7a-hexahydro-cyclopenta[e][1,3]oxazin-4-yl)-4-fluoro-phenyl]-amide, 5-Cyano-pyridine-2-carboxylic acid [3-((1R,7aR)-2-(S)-amino-6,6-difluoro-4,7a-bis-fluoromethyl-4,4a,5,6,7,7a-hexahydro-cyclopenta[e][1,3]oxazin-4-yl)-4-fluoro-phenyl]-amide, 5-Chloro-pyridine-2-carboxylic acid [3-((1R,7aR)-2-(S)-amino-6,6-difluoro-4,7a-bis-fluoromethyl-4,4a,5,6,7,7a-hexahydro-cyclopenta[e][1,3]oxazin-4-yl)-4-fluoro-phenyl]-amide, 5-(1,1-Difluoro-ethyl)-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-(2,2-Difluoro-ethoxy)-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-(2,2-Difluoro-ethoxy)-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 3,5-Dichloro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, and 3,5-Difluoro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, or a pharmaceutical acceptable salt thereof.

A certain embodiment of the invention provides a compound of formula I as described herein, selected from the group consisting of 5-Chloro-pyridine-2-carboxylic acid [3-((4S,4aR,7aR)-2-amino-6,6-difluoro-4-methyl-4,4a,5,6,7,7a-hexahydro-cyclopenta[e][1,3]oxazin-4-yl)-4-fluoro-phenyl]-amide, 5-Cyano-pyridine-2-carboxylic acid [3-((4S,4aR,7aR)-2-amino-6,6-difluoro-4-methyl 4,4a,5,6,7,7a-hexahydro-cyclopenta[e][1,3]oxazin-4-yl)-4-fluoro-phenyl]-amide, 5-Cyano-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Chloro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-But-2-ynyloxy-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 3,5-Dichloro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, and 5-Fluoro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, or a pharmaceutical acceptable salt thereof.

A certain embodiment of the invention provides a compound of formula I as described herein, selected from the group consisting of 5-Chloro-pyridine-2-carboxylic acid [3-((4S,4aR,7aR)-2-amino-6,6-difluoro-4-methyl-4,4a,5,6,7,7a-hexahydro-cyclopenta[e][1,3]oxazin-4-yl)-4-fluoro-phenyl]-amide, and 5-Cyano-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-But-2-ynyloxy-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Cyclopropylmethoxy-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Difluoromethoxy-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Trifluoromethyl-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 3-Chloro-5-trifluoromethyl-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 3-Fluoro-5-trifluoromethyl-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 3-Chloro-5-cyano-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Cyano-3-fluoro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Difluoromethoxy-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Difluoromethyl-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Cyclopropylmethoxy-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Fluoromethoxy-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Trifluoromethyl-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Trifluoromethyl-pyrimidine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 1-Methyl-1H-pyrazole-3-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 4-Chloro-1-difluoromethyl-1H-pyrazole-3-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Cyano-pyridine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Chloro-pyridine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Fluoromethoxy-pyrazine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Chloro-pyrazine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Difluoromethyl-pyrazine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Difluoromethoxy-pyrazine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Methoxy-pyrazine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 4-Chloro-1-difluoromethyl-1H-pyrazole-3-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 2-Methyl-oxazole-4-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-(2,2,2-Trifluoro-ethoxy)-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-(2,2,2-Trifluoro-ethoxy)-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-(2,2,3,3-Tetrafluoro-propoxy)-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-(2,2,3,3,3-Pentafluoro-propoxy)-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Chloro-pyridine-2-carboxylic acid [3-((4S,4aR,7aR)-2-amino-6,6-difluoro-4-methyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Cyano-pyridine-2-carboxylic acid [3-((4S,4aR,7aR)-2-amino-6,6-difluoro-4-methyl 4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Cyano-pyridine-2-carboxylic acid [(S)-3-((1R,2R)-2-amino-6,6-difluoro-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Chloro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Fluoro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 3-Fluoro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Chloro-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Methoxy-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Chloro-pyrimidine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 2-Methyl-oxazole-4-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Cyano-pyridine-2-carboxylic acid [3-((1S,7aS)-2-(R)-amino-6,6-difluoro-4,7a-bis-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Cyano-pyridine-2-carboxylic acid [3-((1R,7aR)-2-(S)-amino-6,6-difluoro-4,7a-bis-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-Chloro-pyridine-2-carboxylic acid [3-((1R,7aR)-2-(S)-amino-6,6-difluoro-4,7a-bis-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-(1,1-Difluoro-ethyl)-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-(2,2-Difluoro-ethoxy)-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 5-(2,2-Difluoro-ethoxy)-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 3,5-Dichloro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a compound of formula I as described herein, which is 3,5-Difluoro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

A certain embodiment of the invention provides a process to synthesize a compound of formula I as described herein, which process comprises reacting a compound of formula XIII with a compound of formula XIV.

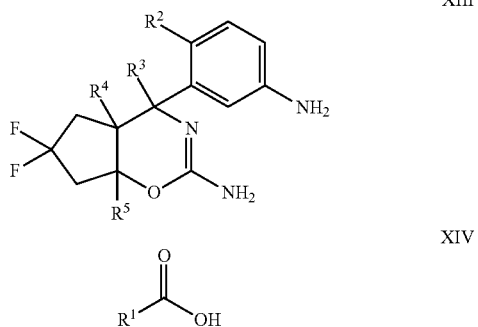

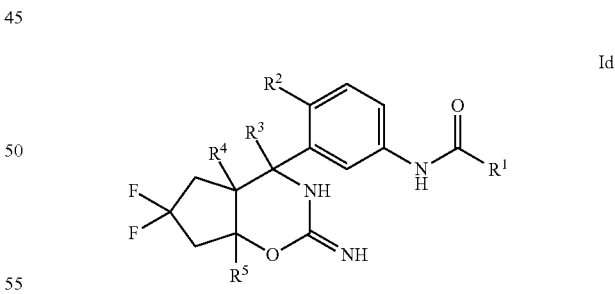

wherein $R^1$, $R^2$, $R^3$, $R^4$, $R^5$ are as described herein.

A certain embodiment of the invention provides a compound of formula I as described herein, whenever prepared by a process as defined above.

A certain embodiment of the invention provides a compound of formula I as described herein for use as therapeutically active substance.

A certain embodiment of the invention provides a compound of formula I as described herein for the use as inhibitor of BACE1 activity.

A certain embodiment of the invention provides a compound of formula I as described herein for the use as therapeutically active substance for the therapeutic and/or prophylactic treatment of diseases and disorders characterized by elevated β-amyloid levels and/or β-amyloid oligomers and/or β-amyloid plaques and further deposits, particularly Alzheimer's disease.

A certain embodiment of the invention provides a compound of formula I as described herein for the use as therapeutically active substance for the therapeutic and/or prophylactic treatment of Alzheimer's disease.

A certain embodiment of the invention provides a pharmaceutical composition comprising a compound of formula I as described herein and a pharmaceutically acceptable carrier and/or a pharmaceutically acceptable auxiliary substance.

A certain embodiment of the invention provides the use of a compound of formula I as described herein for the manufacture of a medicament for the use in inhibition of BACE1 activity.

A certain embodiment of the invention provides the use of a compound of formula I as described herein for the manufacture of a medicament for the use in inhibition of BACE1 activity.

A certain embodiment of the invention provides the use of a compound of formula I as described herein for the manufacture of a medicament for the therapeutic and/or prophylactic treatment of diseases and disorders characterized by elevated β-amyloid levels and/or β-amyloid oligomers and/or β-amyloid plaques and further deposits, particularly Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides a compound of formula I as described herein for the use in inhibition of BACE1 activity.

A certain embodiment of the invention provides a compound of formula I as described herein for the use in the therapeutic and/or prophylactic treatment of diseases and disorders characterized by elevated β-amyloid levels and/or β-amyloid oligomers and/or β-amyloid plaques and further deposits, particularly Alzheimer's disease.

A certain embodiment of the invention provides a compound of formula I as described herein for the use in the therapeutic and/or prophylactic treatment of Alzheimer's disease.

A certain embodiment of the invention provides a method for the use in inhibition of BACE1 activity, particularly for the therapeutic and/or prophylactic treatment of diseases and disorders characterized by elevated β-amyloid levels and/or β-amyloid oligomers and/or β-amyloid plaques and further deposits or Alzheimer's disease, which method comprises administering compound of formula I as described herein to a human being or animal.

Furthermore, the invention includes all optical isomers, i.e. diastereoisomers, diastereomeric mixtures, racemic mixtures, all their corresponding enantiomers and/or tautomers as well as their solvates.

The skilled person in the art will recognize that the compounds of formula I can exist in tautomeric forms, e.g. in the following tautomeric form:

All tautomeric forms are encompassed in the present invention.

The compounds of formula I can contain one or more asymmetric centers and can therefore occur as racemates, racemic mixtures, single enantiomers, diastereomeric mixtures and individual diastereomers. Additional asymmetric centers can be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric centre of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. Certain examples of isomers of a compound of formula I is a compound of formula Ib or a compound of formula Ic, wherein the residues have the meaning as described in any of the embodiments, in particular a compound of formula Ic.

Ib

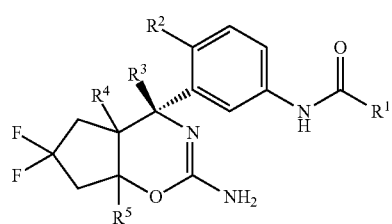

Ic

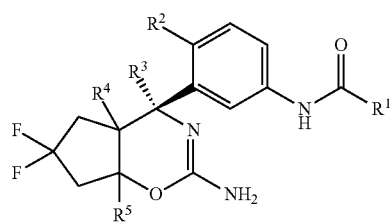

In the embodiments, where optically pure enantiomers are provided, optically pure enantiomer means that the compound contains >90% of the desired isomer by weight, in particular >95% of the desired isomer by weight, or more particular >99% of the desired isomer by weight, said weight percent based upon the total weight of the isomer(s) of the compound. Chirally pure or chirally enriched compounds can be prepared by chirally selective synthesis or by separation of enantiomers. The separation of enantiomers can be carried out on the final product or alternatively on a suitable intermediate.

The compounds of formula I can be prepared in accordance with the following schemes. The starting material is commercially available or can be prepared in accordance with known methods. Any previously defined residues and variables will continue to have the previously defined meaning unless otherwise indicated.

General Scheme 1

The nitro compound (II) is reacted with olefin (III) in the presence of an activating reagent such as e.g. an isocyanate, in particular phenylisocyanate and a catalytic amount of a base, in particular an alkyl amine, more particular $NEt_3$, in a solvent such as benzene or toluene, in particular benzene, or an alkyl ether, in particular diethyl ether to give the dihydroisoxazole (IV).

Fluorination of the dihydroisoxazole (IV) to give the difluoro-dihydroisoxazole (VI) is performed in the presence of a fluorinating agent, in particular morpholinosulfur trifluoride (V) in a solvent in particular an inert solvent, more particular dichloromethane.

The isoxazolidine (VIII) is prepared by reacting an arylhalogenide, in particular an arylbromide, like e.g. arylbromide (VII) with an alkyl lithium reagent, in particular n-BuLi to give an aryllithium species, which can be reacted with the dihydroisoxazole VI in the presence of a Lewis acis, in particular boron trifluoride etherate in a solvent mixture consisting of an ether, in particular THF and toluene at −100° C. to −20° C., in particular at −78° C.

Resolution of the racemic isoxazolidine (VIII) to give the chiral isoxazolidine (IX) can be done by chiral high-performance liquid chromatography (HPLC) using a Chiralpak AD column in a mixture of n-heptane and ethanol.

Hydrogenolysis of the chiral isoxazolidine (IX) to the aminoalcohol (X) can be accomplished best by transfer hydrogenolysis using a Pd-catalyst, in particular Pd on carbon and a hydrogen source, e.g. a salt of formic acid, in particular ammonium formate in a protic solvent such as an alcohol, in particular ethanol.

Oxazine (XI) can be prepared by reaction of aminoalcohol (X) with cyanogen bromide in a solvent such as an alcohol, in particular ethanol at elevated temperature. Alternatively, the reaction can be carried out in two step sequence using cyanogen bromide and a buffer such as e.g. sodium acetate in the presence of a solvent such as e.g. $CH_3CN$ followed by cyclisation of the intermediate in the presence of a mineral acid, in particular hydrochloric acid in a solvent such as an ether, in particular 1,-dioxane.

The nitration of the oxazine (XI) to give the nitro-oxazine (XII) follows a standard procedure involving neat sulfuric acid and fuming nitric acid without using a solvent.

The reduction of the nitro group in the intermediate (XII) to give the aniline (XIII) can be accomplished by hydrogenation using a catalyst such as Pd on carbon in protic solvents, such as alcohols, in particular ethanol or methanol.

Selective amide coupling of the aniline (XIII) and a carboxylic acid (XIV) to give the amide (I') can be effected with 4-(4,6-dimethoxy[1.3.5]triazin-2-yl)-4-methylmorpholinium chloride (DMTMM) hydrate in a solvent such as an alcohol, in particular methanol.

Scheme 1: Synthesis of compounds of formula I with $R^2$ = F, $R^3$ = methyl, $R^4$ = H and $R^5$ = H (I').

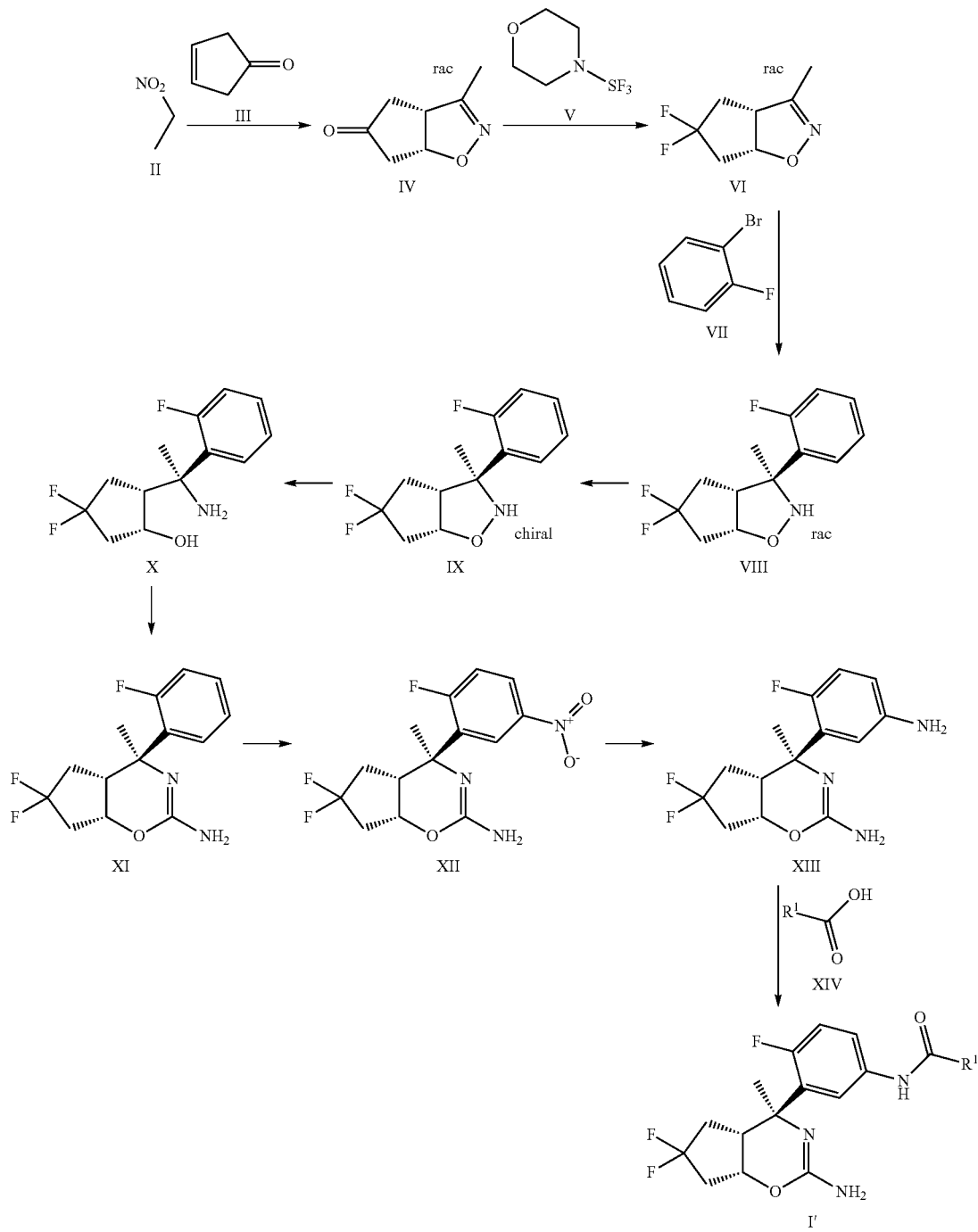

General Scheme 2

(Z)-ethyl 2-chloro-2-(hydroxyimino)acetate (XV) is reacted with olefin (III) in the presence of a base such as e.g. sodium hydrogen carbonate in a solvent such as ethyl acetate to give the dihydroisoxazole (XVI).

Fluorination of the dihydroisoxazole (XVI) to give the difluoro-dihydroisoxazole (XVII) is performed in the presence of a fluorinating agent, in particular morpholinosulfur trifluoride (V) in an inert solvent, in particular dichloromethane.

Reduction of difluoro-dihydroisoxazole (XVII) into alcohol (XVIII) is performed in the presence of a reducing agent in particular sodium borohydride in a protic solvent such as an alcohol, in particular ethanol.

Fluorination of the alcohol (XVIII) to give the trifluoro-dihydroisoxazole (XX) is performed in the presence of a fluorinating agent, in particular bis(2-methoxyethyl)aminosulfur trifluoride (XIX) in an inert solvent, in particular dichloromethane.

The isoxazolidine (XXI) is prepared by reacting an arylhalogenide, in particular an arylbromide, like e.g. arylbromide (VII) with an alkyl lithium reagent, in particular n-BuLi to give an aryllithium species, which can be reacted with the dihydroisoxazole (XX) in the presence of a Lewis acid, in particular boron trifluoride etherate in a solvent mixture consisting of an ether, in particular THF and toluene at −100° C. to −20° C., in particular at −78° C.

Resolution of the racemic isoxazolidine (XXI) to give the chiral isoxazolidine (XXII) can be done by chiral high-performance liquid chromatography (HPLC) using a Chiralpak AD column in a mixture of n-heptane and ethanol.

Hydrogenolysis of the chiral isoxazolidine (XXII) to the aminoalcohol (XXIII) can be accomplished best by transfer hydrogenolysis using a Pd-catalyst, in particular Pd on carbon and a hydrogen source, e.g. a salt of formic acid, in particular ammonium formate, in a protic solvent such as an alcohol, in particular ethanol.

Oxazine (XXIV) can be prepared by reaction of aminoalcohol (XXIII) with cyanogen bromide in a solvent such as an alcohol, in particular ethanol at elevated temperature. Alternatively, the reaction can be carried out in a two step sequence using cyanogen bromide and a buffer such as e.g. sodium acetate in the presence of a solvent such as e.g. $CH_3CN$ followed by cyclisation of the intermediate in the presence of a mineral acid, in particular hydrochloric acid in a solvent such as an ether, in particular 1,4-dioxane.

The nitration of the oxazine (XXIV) to give the nitrooxazine (XXV) follows a standard procedure involving neat sulfuric acid and fuming nitric acid without using a solvent.

The reduction of the nitro group in the intermediate (XXV) to give the aniline (XXVI) can be accomplished by hydrogenation using a catalyst such as Pd on carbon in protic solvents, such as alcohols, in particular ethanol or methanol.

Selective amide coupling of the aniline (XXVI) and a carboxylic acid (XIV) to give the amide I″ can be effected with 4-(4,6-dimethoxy[1.3.5]triazin-2-yl)-4-methylmorpholinium chloride (DMTMM) hydrate in a solvent such as an alcohol, in particular methanol.

Scheme 2: Synthesis of compounds of formula I with $R^2 = F$, $R^3 = CH_2F$, $R^4 = H$ and $R^5 = H$ (I″).

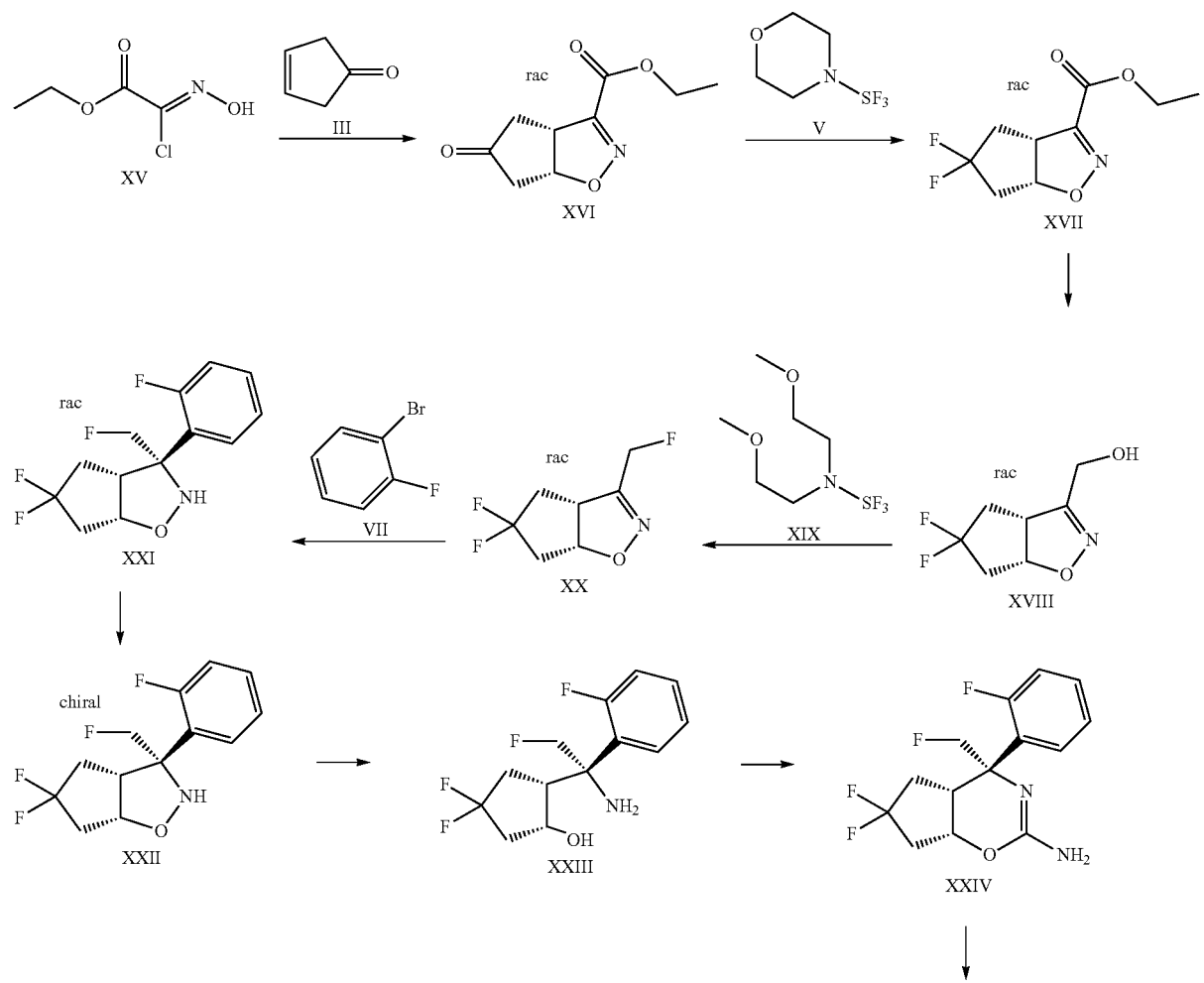

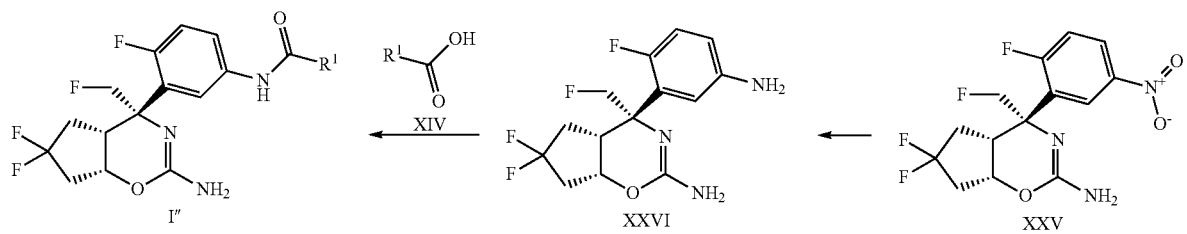

General Scheme 3

The transformation of the primary alcohol (XVIII) to the aldehyde (XXVII) can be achieved by reaction under oxidizing conditions, such as activated dimethylsulfoxide reagents, e.g. prepared from dimethylsulfoxide and oxalyl chloride, in the presence of an amine base, such as triethylamine or diisopropylethylamine, in a chlorinated solvent such as dichloromethane at temperatures from −78° C. to ambient temperature like e.g. 20° C.

Fluorination of the aldehyde (XXVII) to give the tetrafluoro-dihydroisoxazole (XXVIII) is performed in the presence of a fluorinating agent, in particular bis(2-methoxyethyl)aminosulfur trifluoride (XIX), in an inert solvent, in particular dichloromethane.

The isoxazolidine (XXIX) is prepared by reacting an arylhalogenide, in particular an arylbromide, like e.g. arylbromide (VII), with an alkyl lithium reagent, in particular n-BuLi to give an aryllithium species, which can be reacted with the dihydroisoxazole (XXVIII) in the presence of a Lewis acid, in particular boron trifluoride etherate in a solvent mixture consisting of an ether, in particular tetrahydrofuran and toluene at −100° C. to −20° C., in particular at −78° C.

Resolution of the racemic isoxazolidine (XXIX) to give the chiral isoxazolidine (XXX) can be done by chiral high-performance liquid chromatography (HPLC) using a Chiralpak AD column in a mixture of n-heptane and ethanol.

Hydrogenolysis of the chiral isoxazolidine (XXX) to the aminoalcohol (XXXI) can be accomplished best by transfer hydrogenolysis using a Pd-catalyst, in particular Pd on carbon and a hydrogen source, e.g. a salt of formic acid, in particular ammonium formate, in a protic solvent such as an alcohol, in particular ethanol.

Oxazine (XXXII) can be prepared by reaction of aminoalcohol (XXXI) with cyanogen bromide in a solvent such as an alcohol, in particular ethanol at elevated temperature. Alternatively, the reaction can be carried out in a two step sequence using cyanogen bromide and a buffer such as e.g. sodium acetate in the presence of a solvent such as e.g. $CH_3CN$ followed by cyclisation of the intermediate in the presence of a mineral acid, in particular hydrochloric acid in a solvent such as an ether, in particular 1,4-dioxane.

The nitration of the oxazine (XXXII) to give the nitro-oxazine (XXXIII) follows a standard procedure involving neat sulfuric acid and fuming nitric acid without using a solvent.

The reduction of the nitro group in the intermediate (XXXIII) to give the aniline (XXXIV) can be accomplished by hydrogenation using a catalyst such as Pd on carbon in protic solvents, such as alcohols, in particular ethanol or methanol.

Selective amide coupling of the aniline (XXXIV) and a carboxylic acid (XIV) to give the amide (I''') can be effected with 4-(4,6-dimethoxy[1.3.5]triazin-2-yl)-4-methylmorpholinium chloride (DMTMM) hydrate in a solvent such as an alcohol, in particular methanol.

Scheme 3: Synthesis of compounds of formula I with $R^2$ = F, $R^3$ = $CHF_2$, $R^4$ = H and $R^5$ = H (I''').

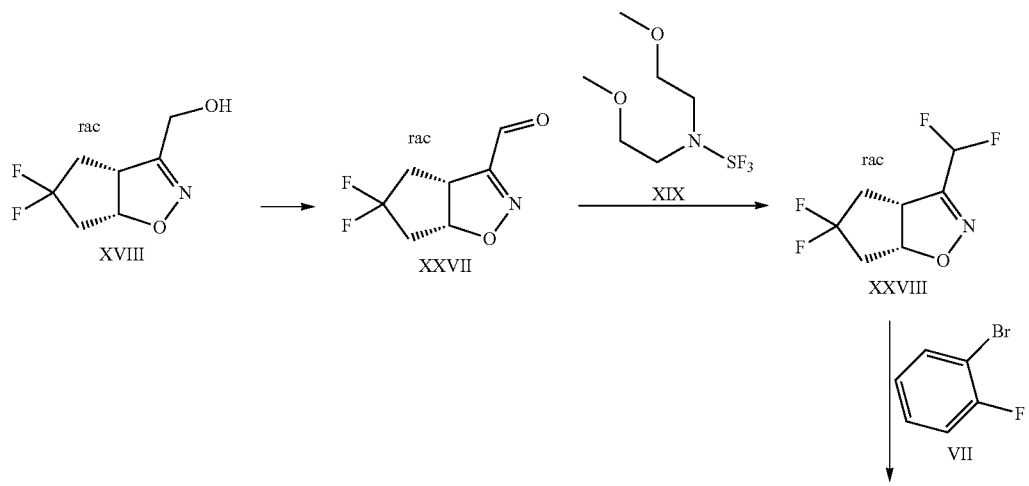

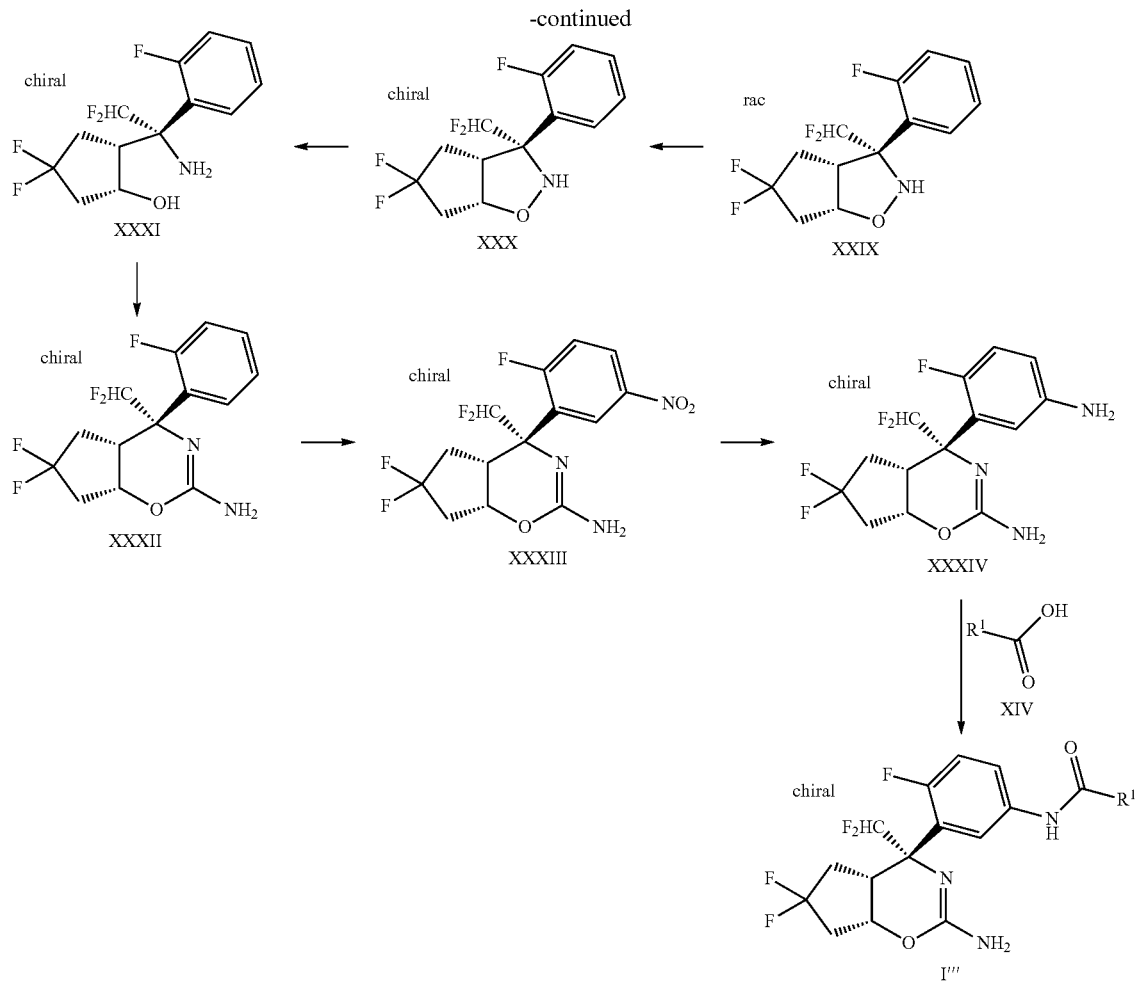

General Scheme 4

(Z)-ethyl 2-chloro-2-(hydroxyimino)acetate (XV) is reacted with olefin (XXXV), in which the primary hydroxy group is preferentially protected with a benzyl and the secondary hydroxyl group is preferentially protected with a tert-butyldimethylsilyl group, in the presence of a base such as e.g. sodium hydrogen carbonate in a solvent such as ethyl acetate to give the dihydroisoxazole (XXXVI).

Removal of the tert-butyldimethylsilyl group of the secondary alcohol in dihydroisoxazole (XXXVI) can be achieved by treatment with a fluoride source such as tetrabutylammonium fluoride in a solvent such as tetrahydrofuran at temperatures between 0 and 50° C., preferably at ambient temperature, to the alcohol (XXXVII).

The transformation of the secondary alcohol (XXXVII) to the ketone XXXVIII can be achieved by reaction under oxidizing conditions, such as activated dimethylsulfoxide reagents, e.g. prepared from dimethylsulfoxide and oxalyl chloride, N-chlorosuccinimide or sulfurtrioxide-pyridine complex, in the presence of an amine base, such as triethylamine or diisopropylethylamine, in a chlorinated solvent such as dichloromethane at temperatures from −78° C. to ambient temperature like e.g. 20° C.

Fluorination of the ketone (XXXVIII) to give the difluoro-dihydroisoxazole (XXXIX) is performed in the presence of a fluorinating agent, in particular morpholinosulfur trifluoride (V) in an inert solvent, in particular dichloromethane.

Reduction of difluoro-dihydroisoxazole (XXXIX) into alcohol (XL) is performed in the presence of a reducing agent in particular sodium borohydride in a protic solvent such as an alcohol, in particular ethanol.

Removal of the benzyl group of the primary alcohol in alcohol (XL) can be achieved by treatment with a strong Lewis acidic reagent, such as boron trichloride, in a chlorinated solvent such as dichloromethane at temperatures between −78° C. and ambient temperature, preferably from −78° C. warming up to 0° C., to the diol (XLI).

Difluorination of the diol (XLI) to give the tetrafluoro-dihydroisoxazole (XLII) is performed in the presence of a fluorinating agent, in particular bis(2-methoxyethyl)amino-sulfur trifluoride (XIX) in an inert solvent, in particular dichloromethane.

The isoxazolidine (XLIII) is prepared by reacting an aryl-halogenide, in particular an arylbromide, like e.g. arylbromide (VII), with an alkyl lithium reagent, in particular n-BuLi to give an aryllithium species, which can be reacted with the dihydroisoxazole (XLII) in the presence of a Lewis acid, in particular boron trifluoride etherate in a solvent mixture consisting of an ether, in particular THF and toluene at −100° C. to −20° C., in particular at −78° C.

Resolution of the racemic isoxazolidine (XLIII) to give the chiral isoxazolidine (XLIVa) can be done by chiral high-performance liquid chromatography (HPLC) using a Chiral-pak AD column in a mixture of n-heptane and ethanol.

Hydrogenolysis of the chiral isoxazolidine (XLIVa) to the aminoalcohol (XLVa) can be accomplished best by transfer hydrogenolysis using a Pd-catalyst, in particular Pd on carbon and a hydrogen source, e.g. a salt of formic acid, in particular ammonium formate in a protic solvent such as an alcohol, in particular ethanol.

Oxazine (XLVIa) can be prepared by reaction of aminoalcohol (XLVa) with cyanogen bromide in a solvent such as an alcohol, in particular ethanol at elevated temperature. Alternatively, the reaction can be carried out in two step sequence using cyanogen bromide and a buffer such as e.g. sodium acetate in the presence of a solvent such as e.g. acetonitrile followed by cyclization of the intermediate in the presence of a mineral acid, in particular hydrochloric acid in a solvent such as an ether, in particular 1,4-dioxane.

The nitration of the oxazine (XLVIa) to give the nitro-oxazine (XLVIIa) follows a standard procedure involving neat sulfuric acid and fuming nitric acid without using a solvent.

The reduction of the nitro group in the intermediate (XLVIIa) to give the aniline (XLVIIIa) can be accomplished by hydrogenation using a catalyst such as Pd on carbon in protic solvents, such as alcohols, in particular ethanol or methanol.

Selective amide coupling of the aniline (XLVIIIa) and a carboxylic acid (XIV) to give the amide (I'''') can be effected with 4-(4,6-dimethoxy[1.3.5]triazin-2-yl)-4-methylmorpholinium chloride (DMTMM) hydrate in a solvent such as an alcohol, in particular methanol.

Scheme 4: Synthesis of compounds of formula I with $R^2 = F$, $R^3 = CH_2F$, $R^4 = H$ and $R^5 = CH_2F$ (I'''').

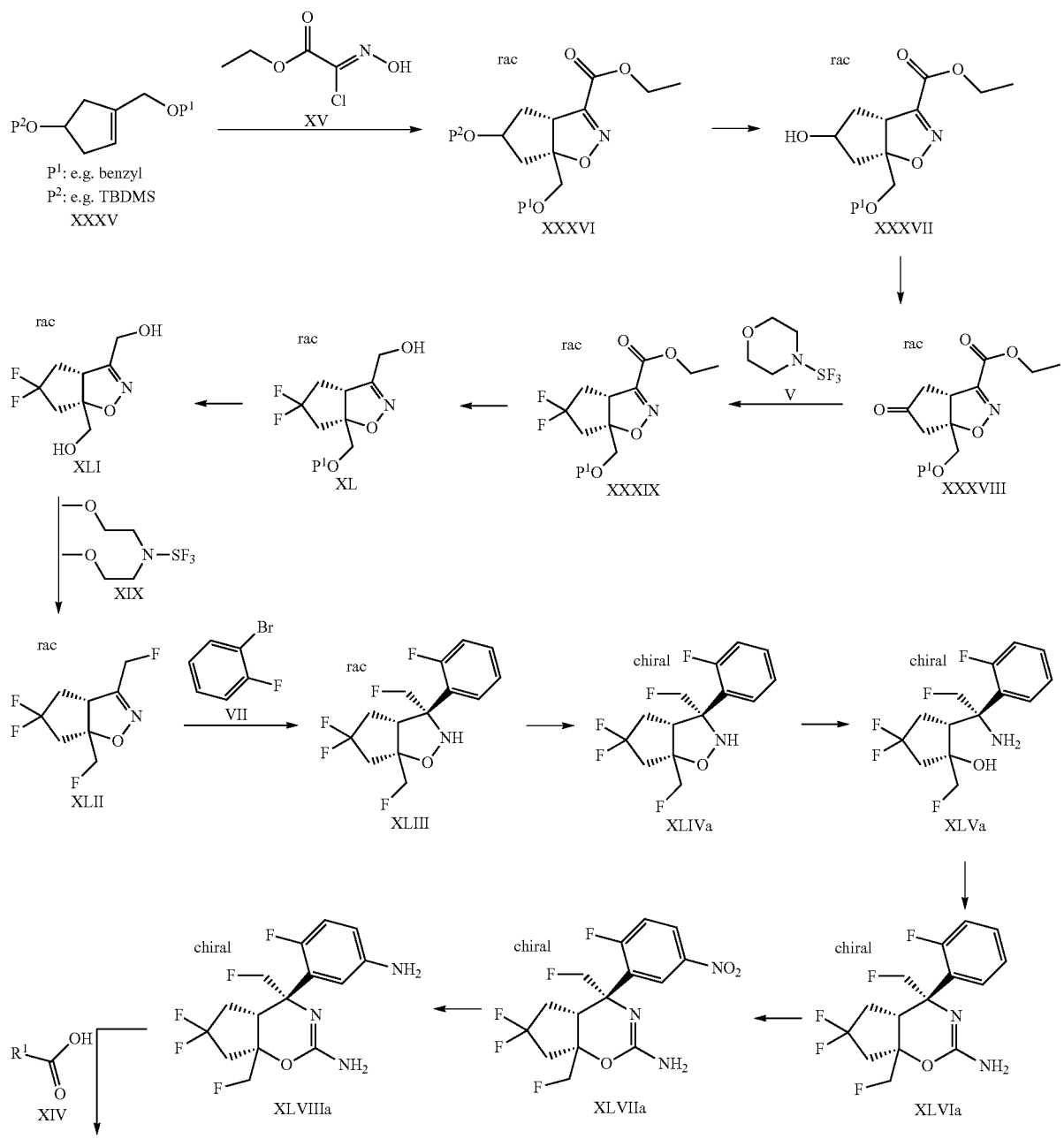

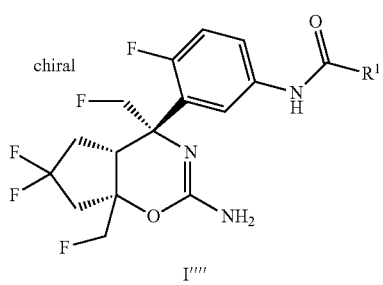

I''''

The corresponding pharmaceutically acceptable salts with acids can be obtained by standard methods known to the person skilled in the art, e.g. by dissolving the compound of formula I in a suitable solvent such as e.g. dioxane or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

Insofar as their preparation is not described in the examples, the compounds of formula I as well as all intermediate products can be prepared according to analogous methods or according to the methods set forth herewithin. Starting materials are commercially available, known in the art or can be prepared by methods known in the art or in analogy thereto.

It will be appreciated that the compounds of formula I in this invention can be derivatized at functional groups to provide derivatives which are capable of conversion back to the parent compound in vivo.

Pharmacological Tests

The compounds of formula I and their pharmaceutically acceptable salts possess valuable pharmacological properties. The compounds of the present invention are associated with inhibition of BACE1 activity. The compounds were investigated in accordance with the test given hereinafter.

Cellular Aβ-Lowering Assay:

Human HEK293 cells which are stably transfected with a vector expressing a cDNA of the human APP wt gene (APP695) were used to assess the potency of the compounds in a cellular assay. The cells were seeded in 96-well microtiter plates in cell culture medium (Iscove, plus 10% (v/v) fetal bovine serum, glutamine, penicillin/streptomycin) to about 80% confluence and the compounds were added at a 10× concentration in ¹/₁₀ volume of medium without FCS containing 8% DMSO (final concentration of DMSO was kept at 0.8% v/v). After 18-20 hrs incubation at 37° C. and 5% $CO_2$ in a humidified incubator the culture supernatant was harvested for the determination of Aβ40 concentrations. 96 well ELISA plates (e.g., Nunc MaxiSorb) were coated with monoclonal antibody which specifically recognize the C-terminal end of Aβ40 (Brockhaus et al., NeuroReport 9, 1481-1486; 1998). After blocking of non-specific binding sites with e.g. 1% BSA and washing, the culture supernatants were added in suitable dilutions together with a horseradish peroxidase-coupled Aβ detection antibody (e.g., antibody 4G8, Senetek, Maryland Heights, Mo.) and incubated for 5 to 7 hrs. Subsequently the wells of the microtiter plate were washed extensively with Tris-buffered saline containing 0.05% Tween 20 and the assay was developed with tetramethylbenzidine/ $H_2O_2$ in citric acid buffer. After stopping the reaction with one volume 1 N $H_2SO_4$ the reaction was measured in an ELISA reader at 450 nm wavelength. The concentrations of Aβ in the culture supernatants were calculated from a standard curve obtained with known amounts of pure Aβ peptide.

TABLE 1

IC₅₀ values of selected examples

| Exam. | Structure | BACE1 cell act. Aβ40 IC₅₀ [µM] |
|---|---|---|
| 1 | 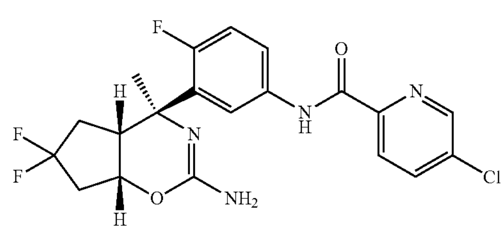 [SMILES: C[C@]1(c2cc(NC(=O)c3ccc(Cl)cn3)ccc2F)N=C(N)O[C@@H]2CC(F)(F)C[C@@H]21] | 0.0004 |

TABLE 1-continued

IC$_{50}$ values of selected examples

| Exam. | Structure | BACE1 cell act. Aβ40 IC$_{50}$ [μM] |
|---|---|---|
| 2 | 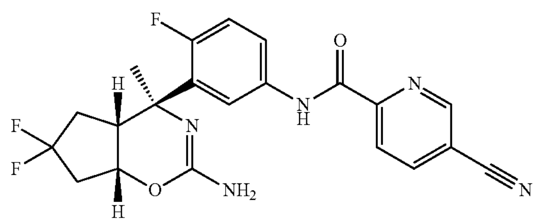 [SMILES: C[C@]1(c2cc(NC(=O)c3ccc(C#N)cn3)ccc2F)N=C(N)O[C@@H]2CC(F)(F)C[C@@H]21] | 0.0017 |
| 3 | 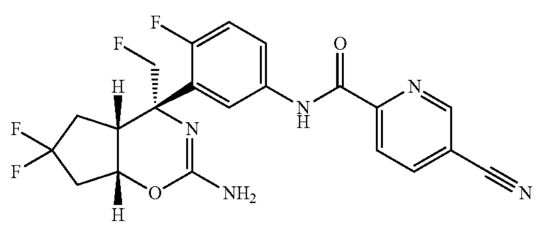 [SMILES: N#Cc1ccc(C(=O)Nc2ccc(F)c([C@@]3(CF)N=C(N)O[C@@H]4CC(F)(F)C[C@@H]43)c2)nc1] | 0.0015 |
| 4 | 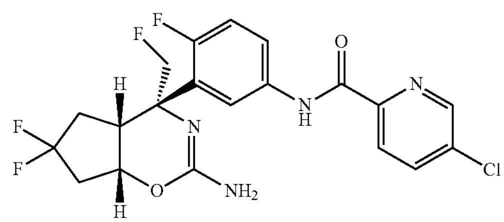 [SMILES: NC1=N[C@](CF)(c2cc(NC(=O)c3ccc(Cl)cn3)ccc2F)[C@H]2CC(F)(F)C[C@H]2O1] | 0.0020 |
| 5 | 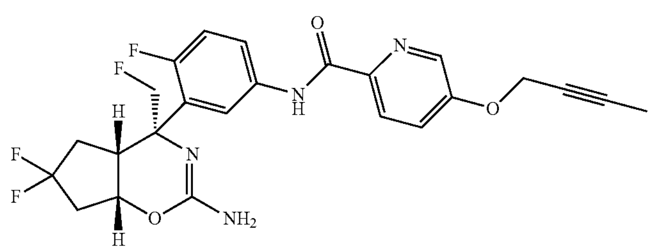 [SMILES: CC#CCOc1ccc(C(=O)Nc2ccc(F)c([C@@]3(CF)N=C(N)O[C@@H]4CC(F)(F)C[C@@H]43)c2)nc1] | 0.0008 |
| 6 | 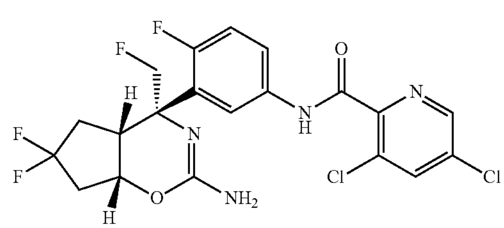 [SMILES: NC1=N[C@](CF)(c2cc(NC(=O)c3ncc(Cl)cc3Cl)ccc2F)[C@H]2CC(F)(F)C[C@H]2O1] | 0.0017 |
| 7 | 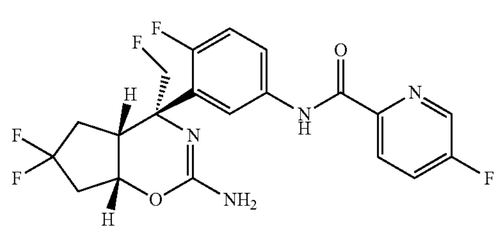 [SMILES: NC1=N[C@](CF)(c2cc(NC(=O)c3ccc(F)cn3)ccc2F)[C@H]2CC(F)(F)C[C@H]2O1] | 0.0166 |

TABLE 1-continued
IC50 values of selected examples
| Exam. | Structure | BACE1 cell act. Aβ40 IC50 [μM] |
|---|---|---|
| 8 | 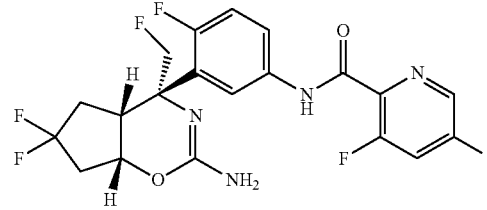 | 0.0169 |
| 9 | 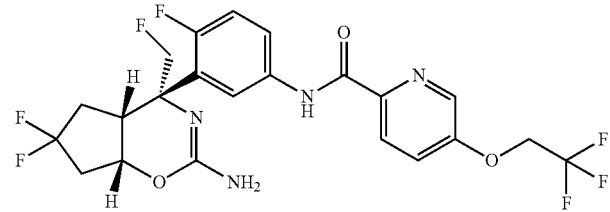 [SMILES: NC1=N[C@](CF)(c2cc(NC(=O)c3ccc(OCC(F)(F)F)cn3)ccc2F)[C@H]2CC(F)(F)C[C@H]2O1] | 0.0170 |
| 10 | 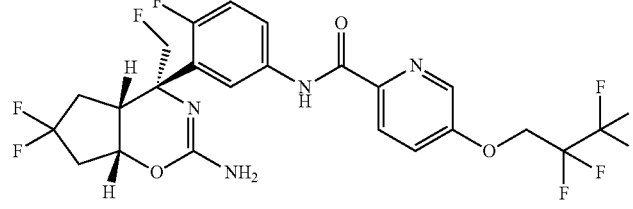 | 0.0430 |
| 11 | 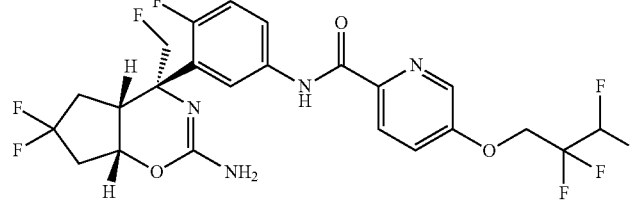 | 0.0140 |
| 12 | 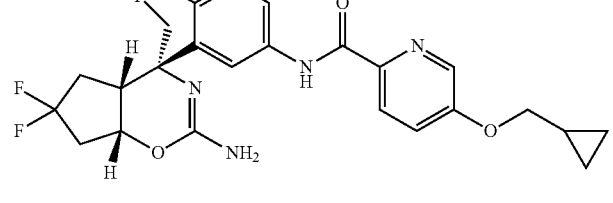 | 0.0086 |
| 13 | 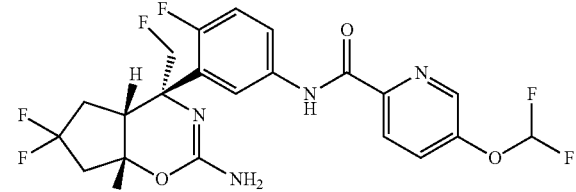 | 0.0035 |

TABLE 1-continued

IC$_{50}$ values of selected examples

| Exam. | Structure | BACE1 cell act. Aβ40 IC$_{50}$ [μM] |
|---|---|---|
| 14 | 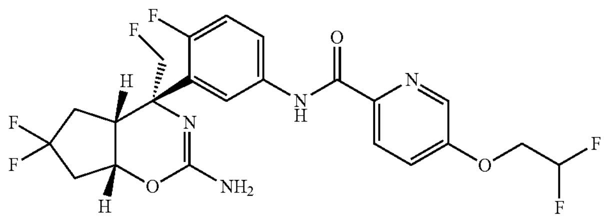 [SMILES: NC1=N[C@](CF)(c2cc(NC(=O)c3ccc(OCC(F)F)cn3)ccc2F)[C@H]2CC(F)(F)C[C@H]2O1] | 0.0230 |
| 15 | 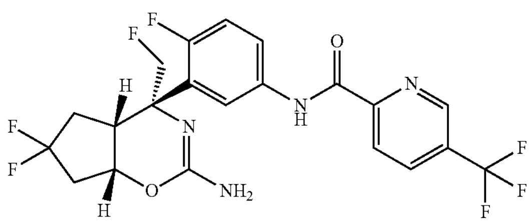 [SMILES: NC1=N[C@](CF)(c2cc(NC(=O)c3ccc(C(F)(F)F)cn3)ccc2F)[C@H]2CC(F)(F)C[C@H]2O1] | 0.0028 |
| 16 | 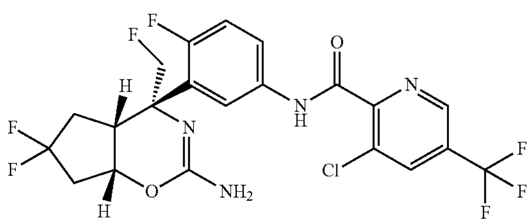 [SMILES: NC1=N[C@](CF)(c2cc(NC(=O)c3ncc(C(F)(F)F)cc3Cl)ccc2F)[C@H]2CC(F)(F)C[C@H]2O1] | 0.0008 |
| 17 | 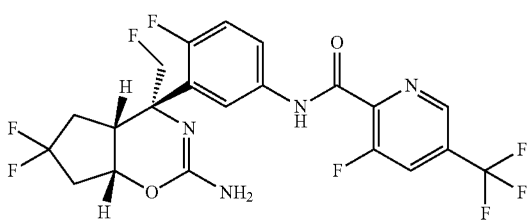 [SMILES: NC1=N[C@](CF)(c2cc(NC(=O)c3ncc(C(F)(F)F)cc3F)ccc2F)[C@H]2CC(F)(F)C[C@H]2O1] | 0.0041 |
| 18 | 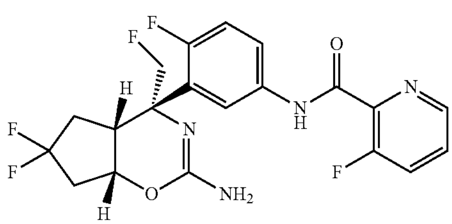 [SMILES: NC1=N[C@](CF)(c2cc(NC(=O)c3ncccc3F)ccc2F)[C@H]2CC(F)(F)C[C@H]2O1] | 0.0270 |
| 19 | 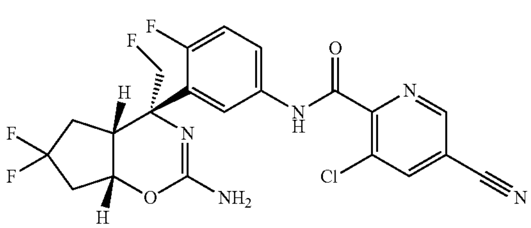 [SMILES: N#Cc1cnc(C(=O)Nc2ccc(F)c([C@@]3(CF)N=C(N)O[C@@H]4CC(F)(F)C[C@@H]43)c2)c(Cl)c1] | 0.0055 |

TABLE 1-continued
IC$_{50}$ values of selected examples
| Exam. | Structure | BACE1 cell act. Aβ40 IC$_{50}$ [μM] |
|---|---|---|
| 20 | 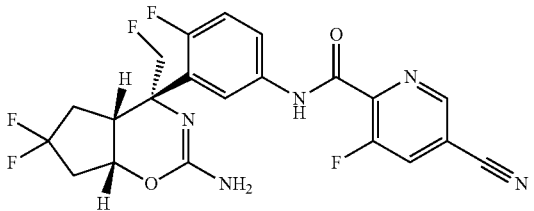 [SMILES: N#Cc1cnc(C(=O)Nc2ccc(F)c([C@@]3(CF)N=C(N)O[C@@H]4CC(F)(F)C[C@@H]43)c2)c(F)c1] | — |
| 21 | 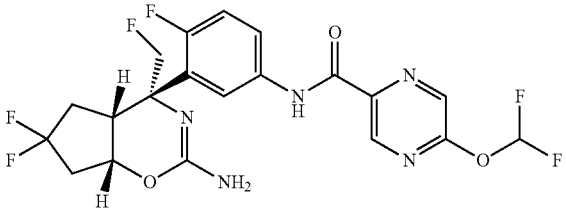 [SMILES: NC1=N[C@](CF)(c2cc(NC(=O)c3cnc(OC(F)F)cn3)ccc2F)[C@H]2CC(F)(F)C[C@H]2O1] | 0.0009 |
| 22 | 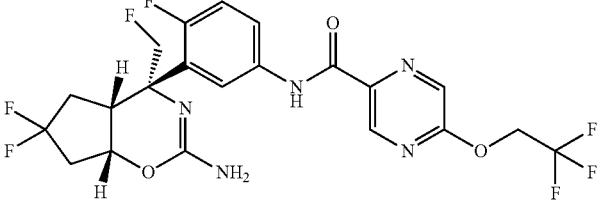 | 0.0025 |
| 23 | 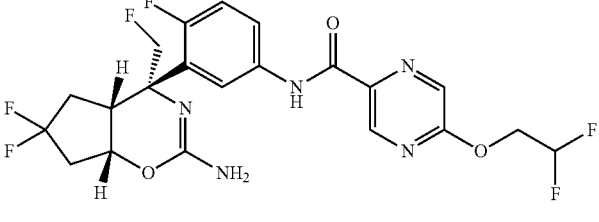 | 0.0078 |
| 24 | 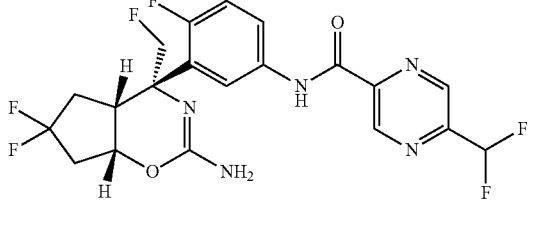 | 0.0079 |
| 25 | 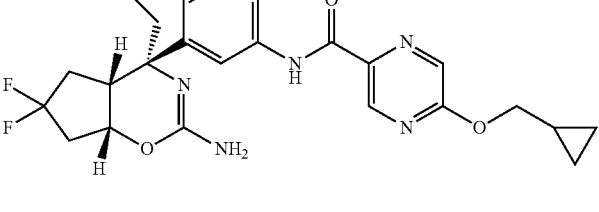 | 0.0150 |

TABLE 1-continued

IC$_{50}$ values of selected examples

| Exam. | Structure | BACE1 cell act. Aβ40 IC$_{50}$ [μM] |
|---|---|---|
| 26 | 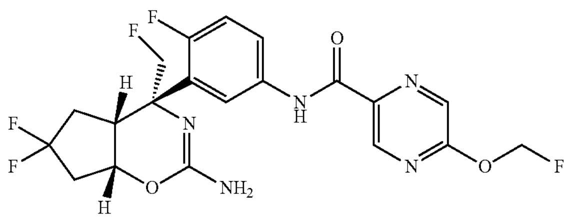 [SMILES: NC1=N[C@](CF)(c2cc(NC(=O)c3cnc(OCF)cn3)ccc2F)[C@H]2CC(F)(F)C[C@H]2O1] | 0.0035 |
| 27 | 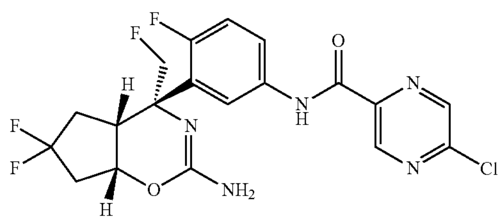 [SMILES: NC1=N[C@](CF)(c2cc(NC(=O)c3cnc(Cl)cn3)ccc2F)[C@H]2CC(F)(F)C[C@H]2O1] | 0.660 |
| 28 | 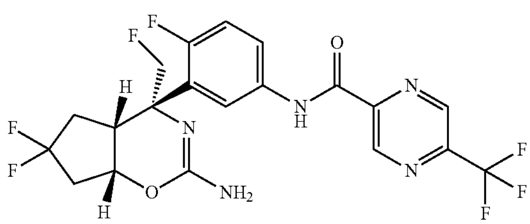 [SMILES: NC1=N[C@](CF)(c2cc(NC(=O)c3cnc(C(F)(F)F)cn3)ccc2F)[C@H]2CC(F)(F)C[C@H]2O1] | 0.0160 |
| 29 | 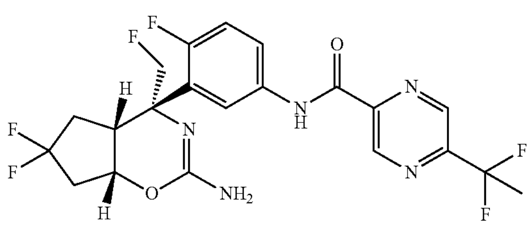 [SMILES: CC(F)(F)c1cnc(C(=O)Nc2ccc(F)c([C@@]3(CF)N=C(N)O[C@@H]4CC(F)(F)C[C@@H]43)c2)cn1] | 0.0360 |
| 30 | 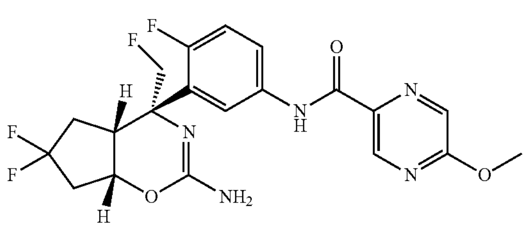 [SMILES: COc1cnc(C(=O)Nc2ccc(F)c([C@@]3(CF)N=C(N)O[C@@H]4CC(F)(F)C[C@@H]43)c2)cn1] | 0.0076 |
| 31 | 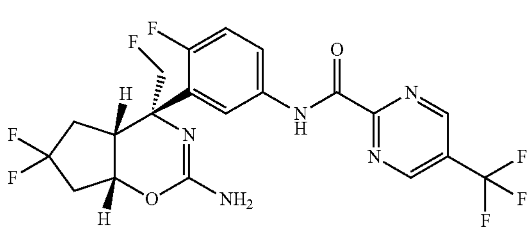 [SMILES: NC1=N[C@](CF)(c2cc(NC(=O)c3ncc(C(F)(F)F)cn3)ccc2F)[C@H]2CC(F)(F)C[C@H]2O1] | 0.0360 |

TABLE 1-continued

IC$_{50}$ values of selected examples

| Exam. | Structure | BACE1 cell act. Aβ40 IC$_{50}$ [μM] |
|---|---|---|
| 32 | 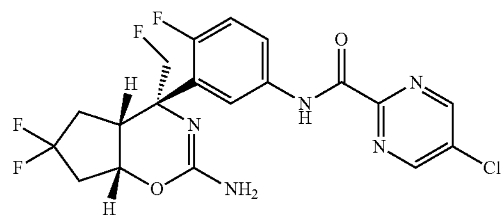 [SMILES: NC1=N[C@](CF)(c2cc(NC(=O)c3ncc(Cl)cn3)ccc2F)[C@H]2CC(F)(F)C[C@H]2O1] | 0.0079 |
| 33 | 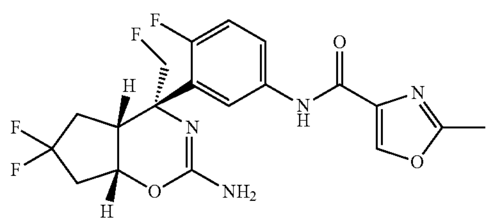 [SMILES: Cc1nc(C(=O)Nc2ccc(F)c([C@@]3(CF)N=C(N)O[C@@H]4CC(F)(F)C[C@@H]43)c2)co1] | 0.0048 |
| 34 | 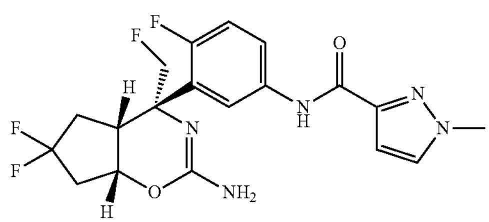 [SMILES: Cn1ccc(C(=O)Nc2ccc(F)c([C@@]3(CF)N=C(N)O[C@@H]4CC(F)(F)C[C@@H]43)c2)n1] | 0.0280 |
| 35 | 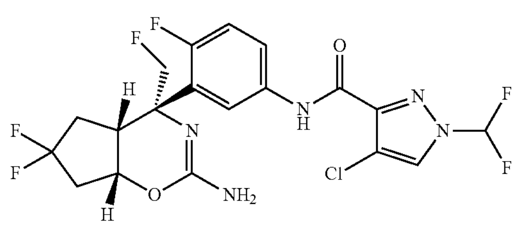 [SMILES: NC1=N[C@](CF)(c2cc(NC(=O)c3nn(C(F)F)cc3Cl)ccc2F)[C@H]2CC(F)(F)C[C@H]2O1] | 0.0030 |
| 36 | 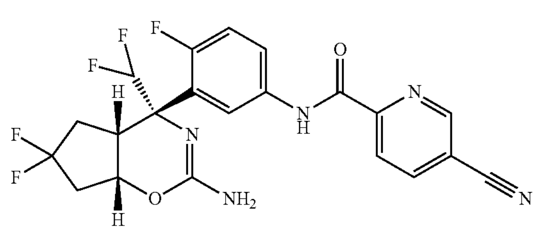 [SMILES: N#Cc1ccc(C(=O)Nc2ccc(F)c([C@@]3(C(F)F)N=C(N)O[C@@H]4CC(F)(F)C[C@@H]43)c2)nc1] | 0.0145 |
| 37 | 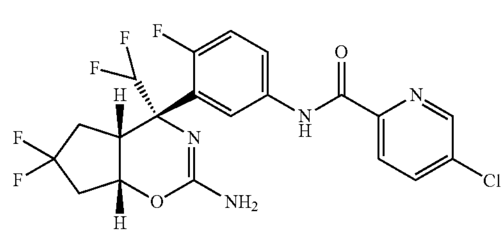 [SMILES: NC1=N[C@@](c2cc(NC(=O)c3ccc(Cl)cn3)ccc2F)(C(F)F)[C@H]2CC(F)(F)C[C@H]2O1] | 0.0170 |

TABLE 1-continued

IC$_{50}$ values of selected examples

| Exam. | Structure | BACE1 cell act. Aβ40 IC$_{50}$ [μM] |
|---|---|---|
| 38 | 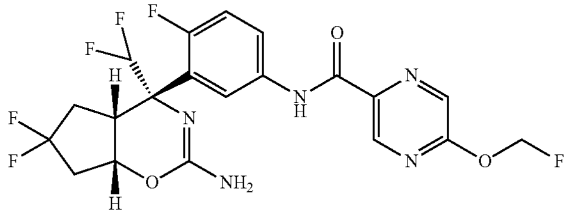 [SMILES: NC1=N[C@@](c2cc(NC(=O)c3cnc(OCF)cn3)ccc2F)(C(F)F)[C@H]2CC(F)(F)C[C@H]2O1] | 0.0170 |
| 39 | 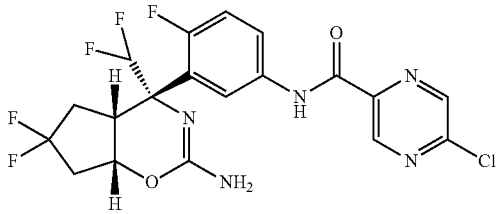 [SMILES: NC1=N[C@@](c2cc(NC(=O)c3cnc(Cl)cn3)ccc2F)(C(F)F)[C@H]2CC(F)(F)C[C@H]2O1] | 1.4000 |
| 40 | 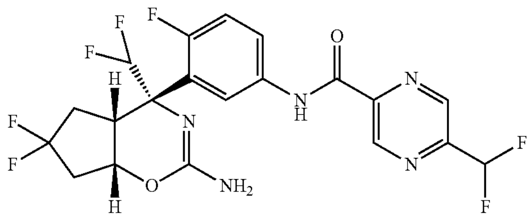 [SMILES: NC1=N[C@@](c2cc(NC(=O)c3cnc(C(F)F)cn3)ccc2F)(C(F)F)[C@H]2CC(F)(F)C[C@H]2O1] | 0.0440 |
| 41 | 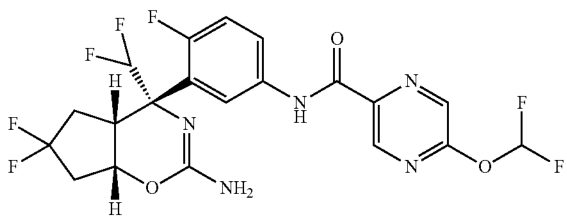 [SMILES: NC1=N[C@@](c2cc(NC(=O)c3cnc(OC(F)F)cn3)ccc2F)(C(F)F)[C@H]2CC(F)(F)C[C@H]2O1] | 0.0070 |
| 42 | 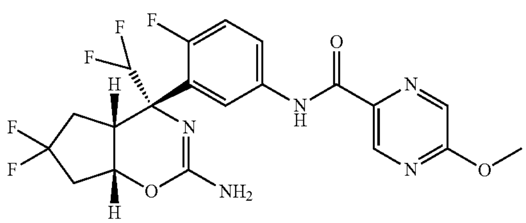 [SMILES: COc1cnc(C(=O)Nc2ccc(F)c([C@@]3(C(F)F)N=C(N)O[C@@H]4CC(F)(F)C[C@@H]43)c2)cn1] | 0.0300 |
| 43 | 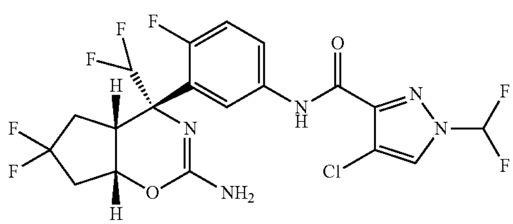 [SMILES: NC1=N[C@@](c2cc(NC(=O)c3nn(C(F)F)cc3Cl)ccc2F)(C(F)F)[C@H]2CC(F)(F)C[C@H]2O1] | 0.0055 |

TABLE 1-continued

IC$_{50}$ values of selected examples

| Exam. | Structure | BACE1 cell act. Aβ40 IC$_{50}$ [μM] |
|---|---|---|
| 44 | 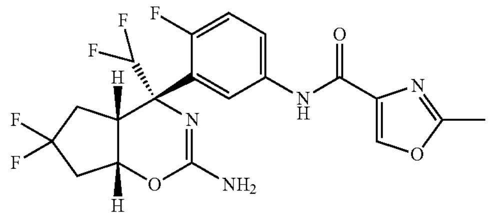 [SMILES: Cc1nc(C(=O)Nc2ccc(F)c([C@@]3(C(F)F)N=C(N)O[C@@H]4CC(F)(F)C[C@@H]43)c2)co1] | 0.0420 |
| 45 | 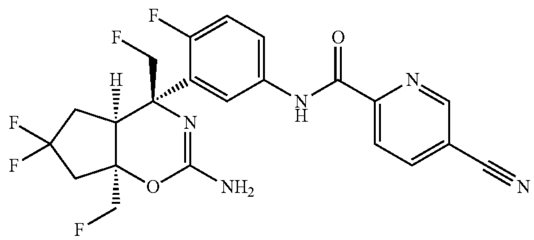 [SMILES: N#Cc1ccc(C(=O)Nc2ccc(F)c([C@]3(CF)N=C(N)O[C@@]4(CF)CC(F)(F)C[C@H]43)c2)nc1] | 11.0500 |
| 46 | 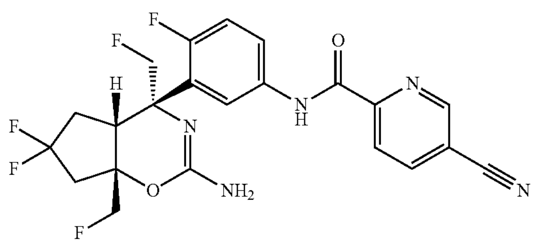 [SMILES: N#Cc1ccc(C(=O)Nc2ccc(F)c([C@@]3(CF)N=C(N)O[C@]4(CF)CC(F)(F)C[C@@H]43)c2)nc1] | 0.0270 |
| 47 | 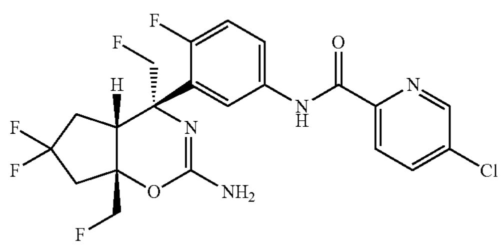 [SMILES: NC1=N[C@](CF)(c2cc(NC(=O)c3ccc(Cl)cn3)ccc2F)[C@H]2CC(F)(F)C[C@@]2(CF)O1] | 0.0850 |

P-gp (P-glycoprotein) Assay

Cell Lines Used for Transport Experiments

The LLC-PK1 cell line (ATCC #CL-101) is a porcine kidney epithelial cell line. The MDR1 (Human multidrug resistance protein 1) transfected cell lines were obtained from Dr. A. Schinkel, The Netherlands Cancer Institute (Amsterdam, The Netherlands). All cell lines were cultured on permeable inserts (96-insert plates Millipore, 0.11 cm$^2$ area, pore size 0.4 μm) at 0.73*10$^6$ cells/ml. Transport measurements were performed at day 4 after seeding. Tightness of the cell monolayer was controlled via the permeability of the extracellular marker lucifer yellow (10 μM). Experiments showing lucifer yellow permeation superior to 25 nm/s were rejected.

In Vitro Transport Experiments

Bidirectional transcellular transport using LLC-PK1 and L-MDR1 LLC-PK1 cells exogenously expressing the human MDR1)

The experiments were performed on a TECAN automated liquid handling system. Briefly, medium was removed from all compartments and the medium of receiver side was replaced with culture medium. The trans-cellular transport measurements were initiated by adding the substrate together with extracellular marker lucifer yellow to the donor side. Inhibitors were added to both sides (1 μM elacridar). Transport experiments were performed both in the basolateral-to-apical and apical-to-basolateral directions with 3 wells each. The plates were incubated at 37° C. and 5% CO$_2$ in a Liconic incubator. Samples were taken from the donor and the opposite (acceptor) side after 2 hours incubation. Concentrations of substrate in both compartments were determined by scintillation counting (digoxin) or by LC-MS/MS. The extracellular marker (lucifer yellow) was quantified using a spectrafluor plus reader at 430/535 nm (Ex/Em). In each experiment 3 different inserts were used for each condition and a mean was calculated.

Data Analysis

Bidirectional transcellular transport using LLC-PK1 and L-MDR1 cells

For the transcellular transport, the following equation was used for data evaluation:

$$P_{app} = \frac{1}{A * C_0} * \frac{dQ}{dt}$$

Where $P_{app}$, A, $C_0$, and dQ/dt represent the apparent permeability, the filter surface area, the initial concentration, and the amount transported per time period, respectively. $P_{app}$ values were calculated on the basis of a single time point (2 h). Transport efflux ratios (ER) were calculated as follows:

$$ER = \frac{P_{app}BA}{P_{app}AB}$$

Where $P_{app}BA$ is the permeability value in the basolateral-to-apical direction, and $P_{app}AB$ the permeability value in the apical-to-basolateral direction. $P_{app}$ were not corrected for flux of the extracellular marker lucifer yellow, which was used to assess the quality of the cell monolayers.

CYP Inhibition Assay

Inhibition of cytochromes P450 (CYPs) 2C9, 2D6 and 3A4 was assessed using human liver microsomes and CYP-selective substrate metabolism reactions. 50 µl incubations were made up containing (finally) 0.2 mg/ml pooled human liver microsomes, 5 µM substrate (diclofenac for CYP2C9 [4' hydroxylase], dextromethorphan for CYP2D6 [O-demethylase] or midazolam for CYP3A4 [1' hydroxylase]), 0.25 µL DMSO containing test inhibitor and NADPH regenerating system. Test inhibitor concentrations of 50, 16.7, 5.6, 1.9, 0.6 and 0.2 µM were assessed in singlicate. Incubations were pre-warmed to 37° C. for 10 minutes before initiation by addition of NADPH regenerating system. Incubations were quenched after 5 minutes (20 minutes for dextromethorphan) by addition of 50 µl cold acetonitrile containing 20 ng/ml 4-OH-diclofenac-13C6, 20 ng/mL dextrorphan-D3 and 20 ng/mL 1-OH-midazolam-D4. Quenched incubates were stored at −20° C. for at least 1 hour before centrifugation (20,000×g, 20 minutes). Supernatants were removed and diluted 1:1 with water prior to analysis using a RapidFire sample injector system and API4000 mass spectrometer. Peak areas for substrate, metabolite and stable-labelled metabolite standard were determined using MS/MS. The peak area ratios between the metabolite generated by the enzymatic reaction and the internal standard were used in subsequent calculations. The percentage of (DMSO) control activity was calculated for each incubate and $IC_{50}$ values estimated by non-linear regression. Sulfaphenazole, quinidine or ketoconazole were tested in each CYP2C9, CYP2D6 or CYP3A4 inhibition experiment, respectively, to ensure assay sensitivity and reproducibility. (Validated assays for human cytochrome P450 activities, R. L. Walsky and R. S. Obach, Drug Metabolism and Disposition 32: 647-660, 2004. and S. Fowler and H. Zhang, The AAPS Journal, Vol. 10, No. 2, 410-424, 2008.)

PatchXpress hERG Inhibition Assay

The detailed method to quantify hERG channel inhibition by the automated patch clamp system PatchXpress® 7000A (Molecular Devices, Sunnyvale, Calif.) has been described by Guo et al. (*J of Pharmacol & Tox Methods*, (2005) 52(1): 123-35). In brief, Chinese hamster ovary (CHO) cells transfected with the human ether-a-go-go-related gene (hERG) was cultured in Ex-cell 302 media supplemented with 10% fetal bovine serum, 2 mM glutamine and 0.25 mg/ml geneticin and maintained in a $CO_2$ incubator at 37° C. For patch clamp electrophysiology, the external buffer contained (in mM): 150 NaCl, 10 Hepes, 4 KCl, 1.2 $CaCl_2$, 1 $MgCl_2$, pH 7.4 adjusted with HCl and the internal recording solution contained (in mM): 140 KCl, 6 EGTA, 5 Hepes, $MgCl_2$, 5 ATP-$Na_2$, pH 7.2 adjusted with KOH. Once the cell was loaded in the recording chamber and formed a giga ohm seal with the planar glass electrodes (Sealchip™), a whole-cell configuration was achieved by rupturing the cell membrane. The membrane potential was then clamped at −80 mV and the hERG channel activated by a 1-second depolarizing pulse delivered at 0.1 Hz, the hERG current was measured during the 500 ms-repolarizing pulse to −40 mV. After an acceptable hERG current recording was obtained, the cell was first exposed to 0.3% DMSO as the vehicle control, followed by the test article in three ascending, full-log interval concentrations and finally E-4031 at 1 µM (as the positive control) to block the hERG current completely. Each test article was tested on three or more cells and at concentrations up to 30 µM or the solubility limit determined the BD Gentest™ solubility scanner. The inhibition of hERG current at each concentration was normalized to that recorded in the vehicle control, and fitted with Hill equation to calculate $IC_{20}$ and/or $IC_{50}$.

Cathepsin D and Cathepsin E Fluorescent Substrate Kinetic Assays

General Assay Principle

The MR121 fluorescence assays described below are based on the fact that MR121 forms a non-fluorescent ground state complex with tryptophan. In solution this formation occurs at millimolar concentrations of tryptophan. The mechanism can be used to design a generic biochemical assay for proteases. A substrate peptide is labeled at the N-terminus with tryptophan and at the C-terminus with the fluorophore MR121 (for cathepsin D the 10 amino acid peptide WTSVLMAAPC-MR121 was used; for cathepsin E, MR121-CKLVFFAEDW was used). In absence of protease activity, the substrates remain intact and the MR121 fluorescence is reduced by the high local Trp-concentration. If the substrates are cleaved by the enzymes the MR121 fluorescence is recovered.

Assay Procedure

The fluorescent substrate cathepsin D and cathepsin E kinetic assays were performed at room temperature in 384-well microtiter plates (black with clear flat bottom, non binding surface plates from Corning) in a final volume of 51 µl. The test compounds were serially diluted in DMSO (15 concentrations, ⅓ dilution steps) and 1 µl of diluted compounds were mixed for 10 min with 40 µl of cathepsin D (from human liver, Calbiochem) diluted in assay buffer (100 mM sodium acetate, 0.05% BSA, pH 5.5; final concentration: 200 nM) or with 40 µl of recombinant human cathepsin E (R&D Systems) diluted in assay buffer (100 mM sodium acetate, 0.05% BSA, pH 4.5; final concentration: 0.01 nM). After addition of 10 µl of the cathepsin D substrate WTSVLMAAPC-MR121 diluted in cathepsin D assay buffer (final concentration: 300 nM) or 1 of 10 the cathepsin E substrate MR121-CKLVFFAEDW diluted in cathepsin E assay buffer (final concentration: 300 nM), the plates were strongly shaken for 2 minutes. The enzymatic reaction was followed in a plate: vision reader (Perkin Elmer) (excitation wavelength: 630 nm; emission: 695 nm) for at least 30 minutes in a kinetic measurement detecting an increase of MR121 fluorescence during the reaction time. The slope in the linear range of the kinetic was calculated and the $IC_{50}$ of the test compounds were determined using a four parameter equation for curve fitting.

Detection of Glutathione Conjugates

The assay conditions for the detection of glutathione conjugates follow the procedure described by C. M. Dieckhaus et al.

Results

TABLE 2

Biological data of selected examples

| Ex. | P-gp human [1] | GSH human [2] | hERG [3] | in vivo effect [4] | Cathepsin E $IC_{50}$ [µM] | Cathepsin D $IC_{50}$ [µM] | CYP $IC_{50}$ [µM] [5] | | |
|---|---|---|---|---|---|---|---|---|---|
| | | | | | | | 3A4 | 2D6 | 2C9 |
| 1  | —  | NF | —  | A | 133  | 52   | A | B | A |
| 2  | —  | NF | A  | A | 101  | 120  | A | A | A |
| 3  | A  | NF | B  | A | >200 | >200 | A | A | A |
| 7  | A  | NF | A  | A | 149  | 93   | A | A | A |
| 24 | A  | NF | B  | A | >200 | >200 | A | A | A |
| 36 | A  | NF | B  | A | >200 | >200 | A | A | A |
| 42 | A  | NF | B  | A | >200 | >150 | A | A | A |

[1] Efflux ratio: substrate category: A = no or weak substrate (ER < 3); B = good substrate (3 < ER < 10);
[2] NF = in vitro no significant adduct formation relative to control;
[3] A = less than 20% inhibition @ 1 µM,; B = less than 15% inhibition @ 1 µM
[4] A = less than 50% of control @ 30 mg/kg p.o.;
[5] A = $IC_{50}$ > 10 µM; B = 1 µM < $IC_{50}$ < 10 µM.

Pharmaceutical Compositions

The compounds of formula I and the pharmaceutically acceptable salts can be used as therapeutically active substances, e.g. in the form of pharmaceutical compositions. The pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical compositions. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Pharmaceutical compositions containing a compound of formula I or a pharmaceutically acceptable salt thereof and a therapeutically inert carrier are also an object of the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt thereof. The daily dosage can be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, in particular 1-100 mg, of a compound of formula I. Examples of compositions according to the invention are:

Example A

Tablets of the following composition are manufactured in the usual manner:

TABLE 2 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 3 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 4 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 5 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 6 possible suppository composition

| ingredient | mg/supp. |
|---|---|
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 7 possible injection solution composition

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 8 possible sachet composition

| ingredient | mg/sachet |
|---|---|
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples are provided for illustration of the invention. They should not be considered as limiting the scope of the invention, but merely as being representative thereof.

General Procedure A: Synthesis of the Intermediate Dihydroisoxazole IV

To a stirred solution of the nitro compound II (62.1 mmol) and the olefin III (60.9 mmol) in ether (15 ml) was added triethylamine (NEt₃) (0.6 mmol) followed by the addition of phenylisocyanate (124 mmol) and stirring was continued at 25° C. for 6 days. The suspension was filtered and the filtrate was chromatographed on silica using a mixture of heptane and ethyl acetate (AcOEt) to afford the pure dihydroisoxazole IV.

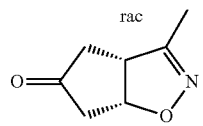

Intermediate IV-1: Starting from nitroethane and cyclopent-3-enone, the product rac (3aR,6aR)-3-Methyl-3a,4,6,6a-tetrahydro-cyclopenta[d]isoxazol-5-one was obtained as a yellow oil.

General Procedure B: Synthesis of the Intermediate Dihydroisoxazole VI

To a stirred solution of the dihydroisoxazole compound IV (12.2 mmol) in dichloromethane (17 ml) at 0° C. was added morpholinosulfur trifluoride V (26.9 mmol) and the solution was stirred at 0° C. for 15 h. The mixture was quenched with a saturated sodium bicarbonate solution. The aqueous reaction mixture was extracted with dichloromethane. The organic layers were washed once with a saturated solution of sodium chloride, dried and evaporated in vacuo. The crude material was purified by Kugelrohr-distillation to afford the pure dihydroisoxazole VI.

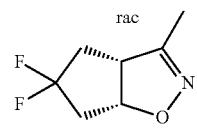

Intermediate VI-1: Starting from rac-(3aR,6aR)-3-methyl-3a,4,6,6a-tetrahydro-cyclopenta[d]isoxazol-5-one, the product rac-(3aR,6aR)-5,5-difluoro-3-methyl-4,5,6,6a-tetrahydro-3aH-cyclopenta[d]isoxazole was obtained as a yellow solid.

General Procedure C: Synthesis of the Intermediate Isoxazolidine VIII and IX

To a stirred solution of the arylbromide VII (13 mmol) in THF (10 ml) and toluene (30 ml) was added at −78° C. n-BuLi (1.6 M in hexane, 7.8 ml) over 10 min and stirring was continued at −78° C. for 1 h.

To a solution of the dihydroisoxazole VI (6.21 mmol) in toluene (70 ml) was added at −78° C. boron trifluoride etherate (BF₃.Et₂O) (12.4 mmol) which was followed by the addition of the phenyllithium reagent prepared above using an insulated cannula over 10 min keeping the temperature below −70° C. The mixture was stirred at −78° C. for 30 min, quenched with saturated aqueous ammonium chloride (NH₄Cl) and extracted with AcOEt. The organic layer was washed with brine, dried, evaporated and the residue was chromatographed on silica using a mixture of cyclohexane and AcOEt to afford the pure isoxazolidine VIII.

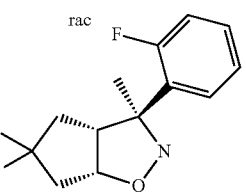

Intermediate VIII-1: Starting from rac-(3aR,6aR)-5,5-difluoro-3-methyl-4,5,6,6a-tetrahydro-3aH-cyclopenta[d]isoxazole, the product rac-(3S,3aR,6aR)-5,5-difluoro-3-(2-fluoro-phenyl)-3-methyl-hexahydro-cyclopenta[d]isoxazole was obtained as a light yellow solid. MS: m/z=258.2 [M+H]⁺.

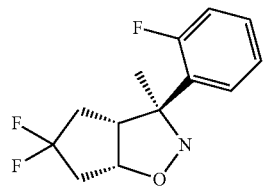 [SMILES: C[C@]1(c2ccccc2F)NO[C@@H]2CC(F)(F)C[C@@H]21]

Intermediate IX-1: The racemate of (3S,3aR,6aR)-5,5-difluoro-3-(2-fluoro-phenyl)-3-methyl-hexahydro-cyclopenta[d]isoxazole was resolved on a chiral high-performance liquid chromatography (HPLC) column (Chiralpak AD) using n-heptane/ethanol (85:15) to give (3R,3aS,6aS)-5,5-difluoro-3-(2-fluoro-phenyl)-3-methyl-hexahydro-cyclopenta[d]isoxazole as the faster eluting enantiomer and the desired (3S,3aR,6aR)-5,5-difluoro-3-(2-fluoro-phenyl)-3-methyl-hexahydro-cyclopenta[d]isoxazole as the slower eluting enantiomer. MS: m/z=258.2 [M+H]⁺.

General Procedure D: Synthesis of the Intermediate Aminoalcohol X

To a solution of the isoxazolidine IX (1.52 mmol) in EtOH (8 ml) was added Pd/C (10%, 81 mg) and ammonium formate (767 mg) and stirring of the mixture was continued at 22° C. for 2.5 h. The suspension was filtered, the filtrate evaporated and the residue was partitioned between AcOEt and a saturated aqueous sodium hydrogen carbonate (NaHCO₃) solution. The organic layer was dried, evaporated to afford the pure aminoalcohol X.

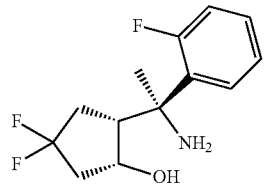 [SMILES: C[C@@](N)(c1ccccc1F)[C@H]1CC(F)(F)C[C@H]1O]

Intermediate X-1: Starting from (3S,3aR,6aR)-5,5-difluoro-3-(2-fluoro-phenyl)-3-methyl-hexahydro-cyclopenta

[d] isoxazole, the product (1R,2R)-2-[(S)-1-amino-1-(2-fluoro phenyl)-ethyl]-4,4-difluoro-cyclopentanol was obtained as a white solid. MS: m/z=260.1 [M+H]⁺.

General Procedure E: Synthesis of the Intermediate Oxazine XI

To a solution of the aminoalcohol X (1.4 mmol) in ethanol (7.5 ml) was added at room temperature a solution of cyanogen bromide (Br—CN) (5M in acetonitrile, 2.85 mmol) and the mixture was heated in a closed reaction tube for 7 h. Ethanol was removed in vacuo. The mixture was partitioned between AcOEt and saturated aqueous sodium carbonate (Na₂CO₃) solution, the organic layer was dried, evaporated and the residue was chromatographed on amine-silica using a mixture of heptane and ethyl acetate (4:1) to afford the pure oxazine XI.

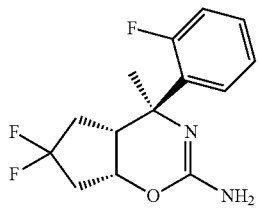 [SMILES: C[C@]1(c2ccccc2F)N=C(N)O[C@@H]2CC(F)(F)C[C@@H]21]

Intermediate XI-1: Starting from (1R,2R)-2-[(S)-1-amino-1-(2-fluoro phenyl)-ethyl]-4,4-difluoro-cyclopentanol, the product (4S,4aR,7aR)-6,6-difluoro-4-(2-fluoro-phenyl)-4-methyl-4,4a,5,6,7,7a-hexahydro-cyclopenta[e][1,3]oxazin-2-ylamine was obtained as a colorless amorphous solid. MS: m/z=285.2 [M+H]⁺.

General Procedure F: Synthesis of the Intermediate Nitro-Oxazine XII

To concentrated sulfuric acid (2 ml) was added portion wise the oxazine XI (0.1 mmol) at 22° C., the solution obtained was cooled to 0° C. and treated with red fuming nitric acid (HNO₃) (0.058 ml) and stiffing was continued at 0° C. for 2 h. The reaction mixture was slowly added to crushed ice, the pH was adjusted to 10 using a saturated sodium carbonate solution, the aqueous layer was extracted with AcOEt, the organic layer was dried and evaporated to afford the pure nitro-oxazine XII.

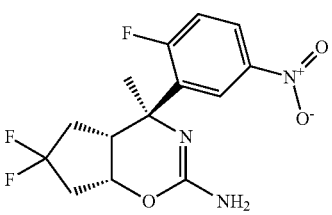 [SMILES: C[C@]1(c2cc([N+](=O)[O-])ccc2F)N=C(N)O[C@@H]2CC(F)(F)C[C@@H]21]

Intermediate XII-1: Starting from (4S,4aR,7aR)-6,6-difluoro-4-(2-fluoro-phenyl)-4-methyl-4,4a,5,6,7,7a-hexahydro-cyclopenta[e][1,3]oxazin-2-ylamine, the product (4S,4aR,7aR)-6,6-difluoro-4-(2-fluoro-5-nitro-phenyl)-4-methyl-4,4a,5,6,7,7a-hexahydro-cyclopenta[e][1,3]oxazin-2-ylamine was obtained as a white solid. MS: m/z=330.2 [M+H]⁺.

General Procedure G: Synthesis of the Intermediate Aniline XIII

A suspension of the nitro-oxazine XII (0.68 mmol) in EtOH (4 ml) and NEt₃ (0.095 ml) was treated with Pd/C (10%, 72 mg) and the mixture was hydrogenated at atmospheric pressure at 22° C. for 1.5 h. The mixture was filtered, the filtrated evaporated to afford the pure aniline XIII.

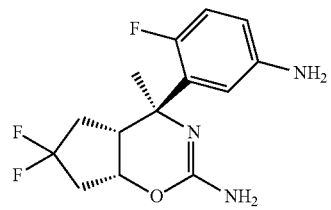 [SMILES: C[C@]1(c2cc(N)ccc2F)N=C(N)O[C@@H]2CC(F)(F)C[C@@H]21]

Intermediate XIII-1: Starting from (4S,4aR,7aR)-6,6-difluoro-4-(2-fluoro-5-nitro-phenyl)-4-methyl-4,4a,5,6,7,7a-hexahydro-cyclopenta[e][1,3]oxazin-2-ylamine, the product (4S,4aR,7aR)-4-(5-amino-2-fluoro-phenyl)-6,6-difluoro-4-methyl-4,4a,5,6,7,7a-hexahydro-cyclopenta[e][1,3]oxazin-2-ylamine was obtained as a white foam. MS: m/z=300.1 [M+H]⁺.

General Procedure H: Synthesis of the Intermediate Dihydroisoxazole XVI

To a solution of the olefin (47.5 mmol) in ethyl acetate (117 ml) were added sodium hydrogen carbonate (238 mmol) and (Z)-ethyl 2-chloro-2-(hydroxyimino)acetate (57.0 mmol). The mixture was vigorously stirred at room temperature over night. An additional equivalent of (Z)-ethyl 2-chloro-2-(hydroxyimino)acetate was added and the mixture was stirred at room temperature for 2 days. The mixture was filtered. The filtrate was washed once with water (120 ml). The aqueous layer was extracted once with ethyl acetate (80 ml). The combined organic layers were dried over sodium sulfate, filtered and concentrated in vacuo. The crude product was purified on silica gel [Eluent: Heptane/ethyl acetate (0 to 30%)] to afford the pure dihydroisoxazole XVI.

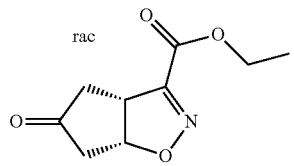

Intermediate XVI-1: Starting from cyclopent-3-enone, the product rac-(3aR,6aR)-5-oxo-4,5,6,6a-tetrahydro-3aH-cyclopenta[d]isoxazole-3-carboxylic acid ethyl ester was obtained as a white solid. MS (m/e): 198.1 (M+H)

General Procedure I: Synthesis of the Intermediate Dihydroisoxazole XVII

To a solution of dihydroisoxazole compound XVI (12.3 mmol) in dichloromethane (24.2 ml) under nitrogen at 0° C., was added morpholinosulfur trifluoride (27.0 mmol). The solution was stirred at 0° C. for 15 hours. The mixture was quenched by dropwise addition of a saturated NaHCO3 solution. The aqueous layer was extracted six times with dichloromethane. The organic layers were washed once with brine, dried with sodium sulfate, filtered and evaporated in vacuo. The crude product was purified on silica gel [Eluent: Heptane/ethyl acetate (0 to 30%)] to afford dihydroisoxazole compound XVII.

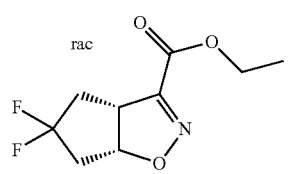

Intermediate XVII-1: Starting from rac-(3aR,6aR)-5-oxo-4,5,6,6a-tetrahydro-3aH-cyclopenta[d]isoxazole-3-carboxylic acid ethyl ester, the product rac-(3aR,6aR)-5,5-difluoro-4,5,6,6a-tetrahydro-3aH-cyclopenta[d]isoxazole-3-carboxylic acid ethyl ester was obtained as a yellow oil. MS (m/e): 220.1 (M+H)

General Procedure J: Synthesis of the Intermediate Dihydroisoxazole XVIII

A solution of dihydroisoxazole XVII (6.39 mmol) in ethanol (26 ml) was cooled to 0° C. Sodium borohydride (12.8 mmol) was added portion wise over a period of 15 minutes, keeping the temperature between 0 and 5° C. After complete addition, the mixture was allowed to warm to room temperature. After 1 hour, sodium borohydride (6.39 mmol) was added at once and the mixture was stirred for 1 hour. Sodium borohydride (6.39 mmol) was added at once and the mixture was stirred for 1 hour. The reaction was cooled in an ice bath. The boranes were destroyed by dropwise addition of HCl 3N (9 ml). The mixture was allowed to warm to room temperature and basified with a 2M Na₂CO₃ solution. The suspension was filtered and the filtrate was concentrated in vacuo. Dichloromethane was added. Both layers were separated and the aqueous layer was extracted three times with dichloromethane. The combined organic layers were dried over sodium sulfate, filtered and concentrated in vacuo. The crude product was purified on silica gel [Eluent: Heptane/ethyl acetate: (0% to 60%)] to afford0dihydroisoxazole compound XVIII.

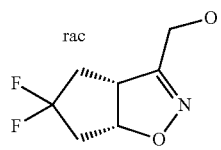 [SMILES: OCC1=NO[C@@H]2CC(F)(F)C[C@H]12]

Intermediate XVIII-1: starting from rac-(3aR,6aR)-5,5-difluoro-4,5,6,6a-tetrahydro-3aH-cyclopenta[d]isoxazole-3-carboxylic acid ethyl ester, the product rac-((3aR,6aR)-5,5-Difluoro-4,5,6,6a-tetrahydro-3 aH-cyclopenta[d] isoxazol-3-yl)-methanol was obtained as a white solid. MS (m/e): 178.1 (M+H)

General Procedure K: Synthesis of the Intermediate Dihydroisoxazole XX

To a solution of dihydroisoxazole XVIII (4.63 mmol) in dichloromethane (16.4 ml) was added dropwise a solution of bis(2-methoxyethyl)aminosulfur trifluoride (5.09 mmol) in dichloromethane (2.05 ml) at −70° C. The light yellow turbid solution was stirred at −70° C. for 30 minutes and then allowed to warm to room temperature. The mixture was stirred for 3 hours. The dark brown solution was cooled in an ice-bath and quenched with a saturated NaHCO3 solution (41 ml) keeping the temperature below 10° C. The mixture was diluted with water (15 ml). The aqueous layer was separated and extracted twice with dichloromethane. The combined organic layers were dried over Na₂SO₄, filtered and concentrated in vacuo. The crude product was purified on silica gel [Eluent: Heptane/ethyl acetate (0% to 30%)] to afford dihydroisoxazole compound XX.

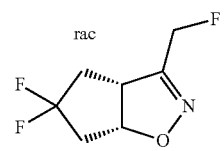

Intermediate XX-1: starting from rac-((3aR,6aR)-5,5-Difluoro-4,5,6,6a-tetrahydro-3aH-cyclopenta[d]isoxazol-3-yl)-methanol, the product rac-(3aR,6aR)-5,5-difluoro-3-fluoromethyl-4,5,6,6a-tetrahydro-3aH-cyclopenta[d]isoxazole was obtained as a white solid. MS (m/e): 180.0 (M+H)

General Procedure L: Synthesis of the Intermediate Isoxazolidine XXI and XXII

To a solution of arylbromide VII (3.52 mmol) in tetrahydrofuran (2.5 ml) and toluene (7.5 ml) was added dropwise under inert atmosphere at −78° C. n-butyllithium 1.6M in hexane (3.35 mmol), keeping the temperature below −70° C. After complete addition the light yellow solution was stirred at −75° C. for 45 minutes. In a second flask dihydroisoxazole compound XX (1.67 mmol) was dissolved in toluene (25 ml). The solution was cooled to −78° C. Boron trifluoride diethyl etherate (3.35 mmol) was added drop wise. The mixture became turbid. The phenyl lithium solution prepared above was added via a dry-ice cooled cannula over a period of 10 minutes. The light yellow solution was stirred at −78° C. for 45 minutes. The mixture was quenched at −70° C. with a 20% NH₄Cl solution (2 ml) and allowed to warm to room temperature. The mixture was diluted with a 20% NH₄Cl solution (25 ml). The aqueous layer was separated and extracted twice with ethyl acetate. The combined organic layers were washed once with brine, dried over Na₂SO₄, filtered and concentrated in vacuo. The crude product was purified on silica gel [Eluent: Heptane/ethyl acetate (0% to 20%)] to afford pure isoxazolidine XXI.

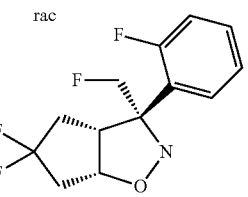

Intermediate XXI-1: Starting from rac-(3aR,6aR)-5,5-difluoro-3-fluoromethyl-4,5,6,6a-tetrahydro-3aH-cyclopenta[d]isoxazole, the product rac-(3S,3aR,6aR)-5,5-Difluoro-3-fluoromethyl-3-(2-fluoro-phenyl)-hexahydro-cyclopenta[d]isoxazole was obtained as a light yellow solid. MS: m/z=276.1 [M+H]⁺.

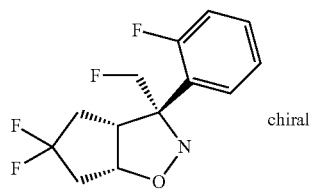 [SMILES: FC[C@]1(c2ccccc2F)NO[C@@H]2CC(F)(F)C[C@@H]21]

chiral

Intermediate XXII-1: The racemate of (3S,3aR,6aR)-5,5-difluoro-3-fluoromethyl-3-(2-fluoro-phenyl)-hexahydro-cyclopenta[d]isoxazole was resolved on a chiral high-performance liquid chromatography (HPLC) column (Chiralpak AD) using n-heptane/ethanol (85:15) to give (3R,3aS,6aS)-5,5-difluoro-3-fluoromethyl-3-(2-fluoro-phenyl)-hexahydro-cyclopenta[d]isoxazole as the faster eluting enantiomer and the desired (3S,3aR,6aR)-5,5-difluoro-3-fluoromethyl-3-(2-fluoro-phenyl)-hexahydro-cyclopenta[d]isoxazole as the slower eluting enantiomer. MS: m/z=276.1 [M+H]$^+$.

General Procedure M: Synthesis of the Intermediate Aminoalcohol XXIII

To a solution of isoxazolidine XXII (2.07 mmol) in ethanol (12 ml) were added Palladium on charcoal 10% (100 mg) and ammonium formate (16.6 mmol). The mixture was stirred at room temperature for 5 hours and filtered through a membrane filter. The filtrate was concentrated in vacuo. The residue was dissolved in ethyl acetate (15 ml). The solution was washed once with a sat. NaHCO$_3$ solution. The aqueous layer was back-extracted once with ethyl acetate. The combined organic layers were dried over Na$_2$SO$_4$, filtered and concentrated in vacuo. The crude product was purified on Si—NH$_2$ [Eluent: Heptane/ethyl acetate (0% to 50%)] to afford pure aminoalcohol XXIII.

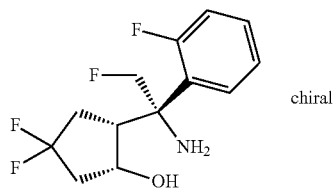 [SMILES: N[C@](CF)(c1ccccc1F)[C@H]1CC(F)(F)C[C@H]1O]

chiral

Intermediate XXIII-1: Starting from (3S,3aR,6aR)-5,5-difluoro-3-fluoromethyl-3-(2-fluoro-phenyl)-hexahydro-cyclopenta[d]isoxazole, the product (1R,2R)-2-[(S)-1-Amino-2-fluoro-1-(2-fluoro-phenyl)-ethyl]-4,4-difluoro-cyclopentanol was obtained as a white solid. MS: m/z=278.0 [M+H]$^+$.

General Procedure N: Synthesis of the Intermediate Oxazine XXIV

To a solution of aminoalcohol XXIII (1.93 mmol) in ethanol (10 ml) was added cyanogene bromide 5M in acetonitrile (2.9 mmol) under nitrogen. The mixture was heated in an 80° C. oil-bath for 19 hours. The solvent was removed in vacuo. The residue was dissolved in ethyl acetate and washed with a 2M Na$_2$CO$_3$ solution. The aqueous layer was extracted once with ethyl acetate. The combined extracts were dried over Na$_2$SO$_4$, filtered and concentrated in vacuo. The crude product was purified on silica gel [Eluent: Heptane/ethyl acetate (0% to 100%)] to afford the pure oxazine XXIV.

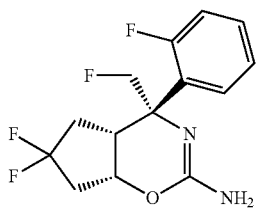 [SMILES: NC1=N[C@](CF)(c2ccccc2F)[C@H]2CC(F)(F)C[C@H]2O1]

Intermediate XXIV-1: Starting from (1R,2R)-2-[(S)-1-amino-2-fluoro-1-(2-fluoro-phenyl)-ethyl]-4,4-difluoro-cyclopentanol, the product (4S,4aR,7aR)-6,6-difluoro-4-fluoromethyl-4-(2-fluoro-phenyl)-4,4a,5,6,7,7a-hexahydro-cyclopenta[e][1,3]oxazin-2-ylamine was obtained as a white solid. MS: m/z=303.2 [M+H]$^+$.

General Procedure O: Synthesis of the Intermediate Nitro-Oxazine XXV

Oxazine XXIV (1.27 mmol) was dissolved in sulfuric acid (10.2 g, 5.57 ml, 102 mmol, Eq: 80). The light yellow solution was cooled in an ethanol/ice bath. Nitric acid fuming (1.78 mmol) was added dropwise over a period of 1 minute. The mixture was stirred under ice-bath cooling for 30 minutes and poured carefully onto ice-water (30 ml). The mixture was basified with a 5N NaOH solution and extracted 3 times with ethyl acetate. The combined extracts were dried over Na$_2$SO$_4$, filtered and concentrated in vacuo. The crude product was purified on silica gel [Eluent: Heptane/ethyl acetate (0% to 50%)] to afford the pure nitro-oxazine XXV.

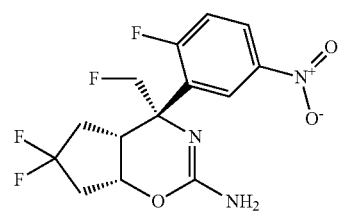 [SMILES: NC1=N[C@](CF)(c2cc([N+](=O)[O-])ccc2F)[C@H]2CC(F)(F)C[C@H]2O1]

Intermediate XXV-1: Starting from (4S,4aR,7aR)-6,6-difluoro-4-fluoromethyl-4-(2-fluoro-phenyl)-4,4a,5,6,7,7a-hexahydro-cyclopenta[e][1,3]oxazin-2-ylamine, the product (4S,4aR,7aR)-6,6-Difluoro-4-fluoromethyl-4-(2-fluoro-5-nitro-phenyl)-4,4a,5,6,7,7a-hexahydro-cyclopenta[e][1,3]oxazin-2-ylamine was obtained as a white solid. MS: m/z=348.1 [M+H]$^+$.

General Procedure P: Synthesis of the Intermediate Aniline XXVI

To a solution of nitro-oxazine XXV (968 µmol) in methanol (7.0 ml) was added palladium on charcoal 10% (34 mg). The mixture was stirred under an hydrogen atmosphere for 30 minutes. The apparatus was purged with argon. The catalyst was filtered off and the filtrate was concentrated in vacuo to afford the pure aniline XXVI.

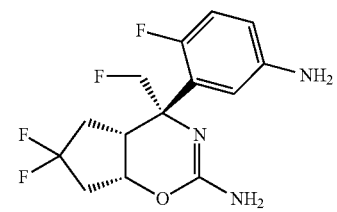 [SMILES: NC1=N[C@](CF)(c2cc(N)ccc2F)[C@H]2CC(F)(F)C[C@H]2O1]

Intermediate XXVI-1: Starting from (4S,4aR,7aR)-6,6-Difluoro-4-fluoromethyl-4-(2-fluoro-5-nitro-phenyl)-4,4a,5,6,7,7a-hexahydro-cyclopenta[e][1,3]oxazin-2-ylamine, the product (4S,4aR,7aR)-4-(5-Amino-2-fluoro-phenyl)-6,6-difluoro-4-fluoromethyl-4,4a,5,6,7,7a-hexahydro-cyclopenta[e][1,3]oxazin-2-ylamine was obtained as a light yellow foam. MS: m/z=318.1 [M+H]⁺.

General Procedure Q for the Synthesis of the Final Examples I

A solution of acid XIV (95.8 µmol) in methanol (720 µl) was cooled to 0° C. 4-(4,6-dimethoxy-1,3,5-triazin-2-yl)-4-methylmorpholinium chloride (125 µmol) was added. After 5 minutes a solution of aniline XIII or XXVI (95.8 µmol) in methanol (240 µl) was added dropwise. The mixture was stirred at 0° C. for 1 hour and then at room temperature over night. The solvent was removed in vacuo. The residue was taken in a saturated NaHCO₃ solution. The solid was filtered, washed with water and dried. The crude product was purified on silica gel (Eluent: Heptane/ethyl acetate (0% to 100%) to provide the final examples of formula I.

General Procedure R: Synthesis of the Intermediate Aldehyde XXVII

To a stirred solution of oxalyl chloride (18.4 mmol) in dichloromethane (40 ml) was added dropwise a solution of dimethylsulfoxide (36.9 mmol) in dichloromethane (7.00 ml) at −60° C. The mixture was stirred for 5 minutes and a solution of the alcohol XVIII (16.8 mmol) in dichloromethane (30.0 ml) was added dropwise. The turbid mixture was stirred for 15 minutes. Triethylamine (83.8 mmol) was added dropwise and the mixture was allowed to warm to room temperature. Water (70 ml) was added, then the aqueous layer was separated and re-extracted twice with dichloromethane. The combined organic layers were dried over Na₂SO₄, filtered and concentrated in vacuo. The crude oil was purified on silica gel (eluent: n-heptane/ethyl acetate 0% to 50%) to provide the pure aldehyde XXVII.

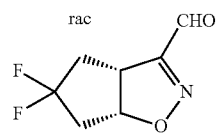 [SMILES: O=CC1=NO[C@@H]2CC(F)(F)C[C@H]12]

Intermediate XXVII-1: Starting from rac-((3aR,6aR)-5,5-difluoro-4,5,6,6a-tetrahydro-3aH-cyclopenta[d]isoxazol-3-yl)-methanol, the product rac-(3aR,6aR)-5,5-difluoro-4,5,6,6a-tetrahydro-3aH-cyclopenta[d]isoxazole-3-carbaldehyde was obtained as a light yellow solid. MS: m/z=175.0[M]⁺.

General Procedure S: Synthesis of the Intermediate Dihydroisoxazole XXVIII

To a solution of the aldehyde XXVII (2.85 mmol) in dichloromethane (5 ml) was added dropwise a solution of bis-(2-methoxyethyl)aminosulfur trifluoride (731 mg, 609 µl, 3.14 mmol) in dichloromethane (2 ml) at 0° C. After 5 minutes, the mixture was allowed to warm to room temperature and stirred for 3 hours. The yellow solution was cooled in an ice-bath and quenched with a saturated NaHCO₃ solution (6.2 ml). The aqueous layer was separated and extracted twice with dichloromethane. The combined organic layers were dried over Na₂SO₄, filtered and concentrated at reduced pressure (room temperature, 300 mbar). The crude product was purified on silica gel (eluent: n-pentane/ether 0% to 30% in 10 minutes). After removal of the solvent at 20° C. and 400 mbar, the concentrated product was dried at 20° C. and 200 mbar.

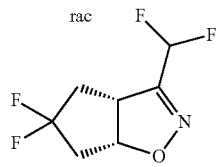 [SMILES: FC(F)C1=NO[C@@H]2CC(F)(F)C[C@H]12]

Intermediate XXVIII-1: Starting from rac-(3aR,6aR)-5,5-difluoro-4,5,6,6a-tetrahydro-3aH-cyclopenta[d]isoxazole-3-carbaldehyde, the product rac-(3aR,6aR)-3-difluoromethyl-5,5-difluoro-4,5,6,6a-tetrahydro-3 aH-cyclopenta[d]isoxazole was obtained as a light yellow liquid. MS: m/z=197 [M]⁺.

Synthesis of the Intermediate Isoxazolidines XXIX and XXX

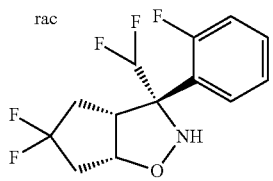 [SMILES: Fc1ccccc1[C@@]1(C(F)F)NO[C@@H]2CC(F)(F)C[C@@H]21]

Intermediate XXIX-1 was obtained following general procedure L: Starting from rac-(3aR,6aR)-3-difluoromethyl-5,5-difluoro-4,5,6,6a-tetrahydro-3aH-cyclopenta[d]isoxazole, the reaction with 1-bromo-2-fluoro-benzene yielded the product rac-(3S,3aR,6aR)-3-difluoromethyl-5,5-difluoro-3-(2-fluoro-phenyl)-hexahydro-cyclopenta[d]isoxazole as a light brown oil. MS: m/z=294.4 [M+H]⁺.

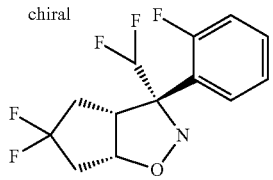 [SMILES: Fc1ccccc1[C@@]1(C(F)F)NO[C@@H]2CC(F)(F)C[C@@H]21]

Intermediate XXX-1 and XXX-2: The racemate of (3S,3aR,6aR)-3-difluoromethyl-5,5-difluoro-3-(2-fluoro-phenyl)-hexahydro-cyclopenta[d]isoxazole was resolved on a chiral high-performance liquid chromatography (HPLC) column (Chiralpak AD) using n-heptane/isopropanol (80:20) as the eluent to give the faster eluting enantiomer (3R,3aS,6a5)-3-(difluoromethyl)-5,5-difluoro-3-(2-fluorophenyl)hexahydro-2H-cyclopenta[d]isoxazole (XXX-1) and the desired (3S,3aR,6aR)-3-(difluoromethyl)-5,5-difluoro-3-(2-fluorophenyl)hexahydro-2H-cyclopenta[d]isoxazole (XXX-2) as the slower eluting enantiomer. Intermediate XXX-1 was obtained as a yellow oil; MS: m/z=294.3 [M+H]⁺. Intermediate XXX-2 was obtained as a colorless oil after dissolution in ethanol and treatment with charcoal; MS: m/z=294.3 [M+H]⁺.

Synthesis of the Intermediate Aminoalcohol XXXI

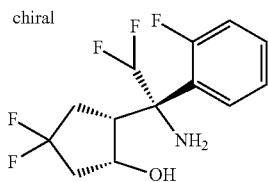 [SMILES: N[C@@](c1ccccc1F)(C(F)F)[C@H]1CC(F)(F)C[C@H]1O]

Intermediate XXXI-1 was obtained following general procedure M: Starting from (3S,3aR,6aR)-3-(difluoromethyl)-5,5-difluoro-3-(2-fluorophenyl)hexahydro-2H-cyclopenta[d]isoxazole (intermediate XXX-2), the reduction with ammonium formate and palladium on charcoal (10%) as the catalyst yielded the product (1R,2R)-2-[(S)-1-amino-2,2-difluoro-1-(2-fluoro-phenyl)-ethyl]-4,4-difluoro-cyclopentanol as a colorless foam. MS: m/z=296.3 [M+H]$^+$.

Synthesis of the Intermediate Oxazine XXXII

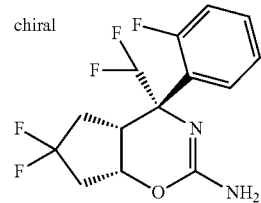 [SMILES: NC1=N[C@@](c2ccccc2F)(C(F)F)[C@H]2CC(F)(F)C[C@H]2O1 ; "chiral"]

Intermediate XXXII-1 was obtained following general procedure N: Starting from (1R,2R)-2-[(S)-1-amino-2,2-difluoro-1-(2-fluoro-phenyl)-ethyl]-4,4-difluoro-cyclopentanol, the product (4S,4aR,7aR)-4-difluoromethyl-6,6-difluoro-4-(2-fluoro-phenyl)-4,4a,5,6,7,7a-hexahydro-cyclopenta[e][1,3]oxazin-2-ylamine was obtained as a white solid. MS: m/z=321.3 [M+H]$^+$.

Synthesis of the Intermediate Nitro-Oxazine XXXIII

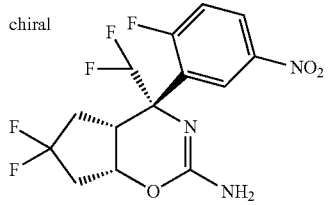 [SMILES: NC1=N[C@@](c2cc([N+](=O)[O-])ccc2F)(C(F)F)[C@H]2CC(F)(F)C[C@H]2O1 ; "chiral"]

Intermediate XXXIII-1 was obtained following general procedure O: Starting from (4S,4aR,7aR)-4-difluoromethyl-6,6-difluoro-4-(2-fluoro-phenyl)-4,4a,5,6,7,7a-hexahydro-cyclopenta[e][1,3]oxazin-2-ylamine, the product (4S,4aR,7aR)-4-difluoromethyl-6,6-difluoro-4-(2-fluoro-5-nitro-phenyl)-4,4a,5,6,7,7a-hexahydro-cyclopenta[e][1,3]oxazin-2-ylamine was obtained as a white foam. MS: m/z=366.3 [M+H]$^+$.

Synthesis of the Intermediate Aniline XXXIV

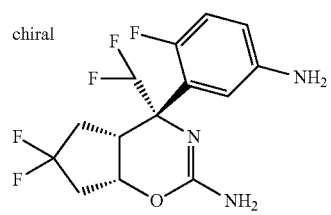 [SMILES: NC1=N[C@@](c2cc(N)ccc2F)(C(F)F)[C@H]2CC(F)(F)C[C@H]2O1 ; "chiral"]

Intermediate XXXIV-1 was obtained following general procedure P: Starting from (4S,4aR,7aR)-4-difluoromethyl-6,6-difluoro-4-(2-fluoro-5-nitro-phenyl)-4,4a,5,6,7,7a-hexahydro-cyclopenta[e][1,3]oxazin-2-ylamine, the product (4S,4aR,7aR)-4-(5-amino-2-fluoro-phenyl)-4-difluoromethyl-6,6-difluoro-4,4a,5,6,7,7a-hexahydro-cyclopenta[e][1,3]oxazin-2-ylamine was obtained as a white foam. MS: m/z=336.3 [M+H]$^+$.

Synthesis of the Intermediate Dihydroisoxazole XXXVI

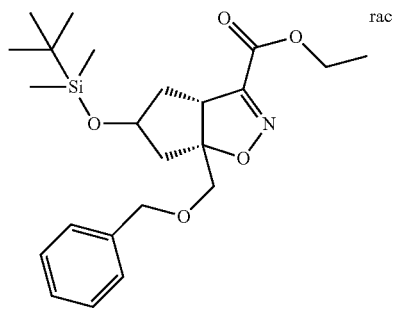

Intermediate XXXVI was obtained following general procedure H: Starting from (3-(benzyloxymethyl)cyclopent-3-enyloxy)(tert-butyl)dimethylsilane and (Z)-ethyl 2-chloro-2-(hydroxyimino)acetate, the diastereoisomers rac-(3aR,5R,6aR)- and rac-(3aR,5S,6aR)-ethyl 6a-(benzyloxymethyl)-5-(tert-butyldimethylsilyloxy)-4,5,6,6a-tetrahydro-3aH-cyclopenta[d]isoxazole-3-carboxylate were obtained as a colorless oil. MS: m/z=434.5 [M+H]$^+$.

The starting material (3-(benzyloxymethyl)cyclopent-3-enyloxy)(tert-butyl)dimethylsilane was obtained as follows:

To a solution of 3-(benzyloxymethyl)cyclopent-3-enol (CAS 153186-83-5; Nucleosides, Nucleotides, and Nucleic Acids 26: 935-37, 2007) (5.75 g, 28.1 mmol) and imidazole (2.87 g, 42.2 mmol) in dry N,N-dimethylformamide (20 ml) at 0° C. was added tert-butyldimethylchlorosilane (5.09 g, 33.8 mmol). Stirring was continued at 0° C. for 5 minutes, the cooling bath was removed and the mixture was stirred at 23° C. for 2 h. For the workup, the reaction mixture was poured into water, followed by extraction with TBME. The organic layer was washed with brine and dried over Na$_2$SO$_4$. Removal of the solvent at reduced pressure left a yellow oil, which was purified by flash chromatography (silica gel, 50 g, 0% to 15% EtOAc in heptane) to give the (3-(benzyloxymethyl)cyclopent-3-enyloxy)(tert-butyl)dimethylsilane (7.3 g, 81.4% yield) as a colorless liquid.

Synthesis of the Intermediate Dihydroisoxazole XXXIX

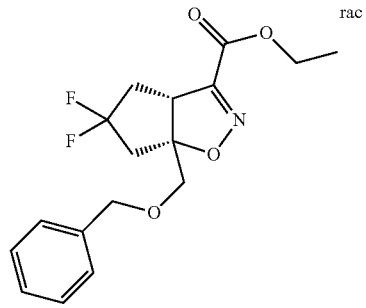

Intermediate XXXIX was obtained following general procedure I: Starting from rac-(3aR,6aR)-ethyl 6a-(benzyloxymethyl)-5-oxo-4,5,6,6a-tetrahydro-3aH-cyclopenta[d]isoxazole-3-carboxylate (XXXVIII), the product rac-(3aR,6aR)-ethyl 6a-(benzyloxymethyl)-5,5-difluoro-4,5,6,6a-tetrahydro-3aH-cyclopenta[d]isoxazole-3-carboxylate was obtained as a colorless oil. MS: m/z=340.1 [M+H]$^+$.

The starting material rac-(3aR,6aR)-ethyl 6a-(benzyloxymethyl)-5-oxo-4,5,6,6a-tetrahydro-3aH-cyclopenta[d]isoxazole-3-carboxylate (XXXVIII) was obtained as follows:

rac-(3aR,5R,6aR)- and rac-(3aR,5S,6aR)-ethyl 6a-(Benzyloxymethyl)-5-hydroxy-4,5,6,6a-tetrahydro-3aH-cyclopenta[d]isoxazole-3-carboxylate (XXXVII).

A solution of rac-(3aR,5R,6aR)- and rac-(3aR,5S,6aR)-ethyl 6a-(benzyloxymethyl)-5-(tert-butyldimethylsilyloxy)-4,5,6,6a-tetrahydro-3aH-cyclopenta[d]isoxazole-3-carboxylate (XXXVI) (6.3 g, 14.5 mmol) in tetrahydrofuran (145 ml) was treated dropwise at 0° C. with a solution of tetrabutylammonium fluoride (1 M in tetrahydrofuran; 21.8 ml, 21.8 mmol). The reaction mixture was left to warm to 23° C. and stirred for 2 hours. For the workup, the reaction mixture was extracted with water and ethyl acetate. The organic layer was separated, dried over sodium sulphate, and evaporated at reduced pressure. The residue was purified by chromatography with a mixture of heptane and ethyl acetate (0-80%) to give a mixture of the 2 diastereoisomers rac-(3aR,5R,6aR)- and rac-(3aR,5S,6aR)-ethyl 6a-(benzyloxymethyl)-5-hydroxy-4,5,6,6a-tetrahydro-3aH-cyclopenta[d]isoxazole-3-carboxylate (3.6 g, 11.3 mmol, 78% yield) as a light yellow oil. rac-(3aR,6aR)-ethyl 6a-(Benzyloxymethyl)-5-oxo-4,5,6,6a-tetrahydro-3aH-cyclopenta[d]isoxazole-3-carboxylate (XXXVIII)

To a solution of rac-(3aR,5R,6aR)- and rac-(3aR,5S,6aR)-ethyl 6a-(benzyloxymethyl)-5-hydroxy-4,5,6,6a-tetrahydro-3aH-cyclopenta[d]isoxazole-3-carboxylate (XXXVII) (3.1 g, 9.71 mmol) in dry dimethylsulfoxide (50 ml) was added at room temperature triethylamine (5.89 g, 8.12 ml, 58.2 mmol) and sulfur trioxide-pyridine complex (4.64 g, 29.1 mmol). The brown solution was stirred at room temperature for 2 hours. For the workup, the reaction mixture was poured on water and extracted twice with ethyl acetate. The organic layers were washed with brine, dried over sodium sulphate, and evaporated at reduced pressure. The residue was purified by chromatography with a mixture of heptane and ethyl acetate (0-50%) to give the rac-(3aR,6aR)-ethyl 6a-(benzyloxymethyl)-5-oxo-4,5,6,6a-tetrahydro-3aH-cyclopenta[d]isoxazole-3-carboxylate (2.4 g, 78% yield) as a light brown oil.

Synthesis of the Intermediate Dihydroisoxazole XL

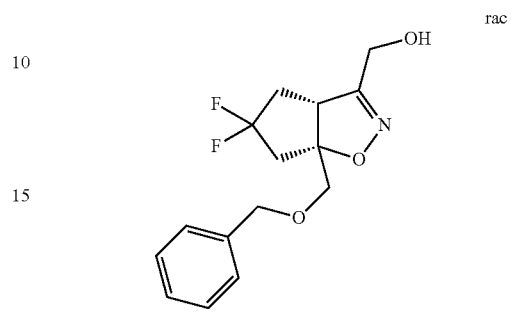

Intermediate XL was obtained following general procedure J: Starting from rac-(3aR,6aR)-ethyl 6a-(benzyloxymethyl)-5,5-difluoro-4,5,6,6a-tetrahydro-3aH-cyclopenta[d]isoxazole-3-carboxylate (XXXIX), the product rac-((3aR,6aR)-6a-(benzyloxymethyl)-5,5-difluoro-4,5,6,6a-tetrahydro-3aH-cyclopenta[d]isoxazol-3-yl)methanol was obtained as a colorless oil. MS: m/z=298.2 [M+H]$^+$.

Synthesis of the Intermediate Dihydroisoxazole XLII

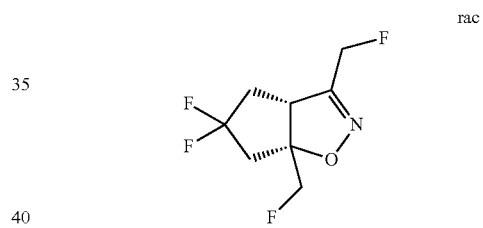

Intermediate XLII was obtained following general procedure K: Starting from rac-((3aR,6aR)-5,5-difluoro-4,5,6,6a-tetrahydro-3aH-cyclopenta[d]isoxazole-3,6a-diyl)dimethanol (XLI), the product rac-(3aR,6aR)-5,5-difluoro-3,6a-bis(fluoromethyl)-4,5,6,6a-tetrahydro-3aH-cyclopenta[d]isoxazole was obtained as a light yellow liquid (in order to complete the reaction, 3 equivalents of the bis(2-methoxyethyl)aminosulfur trifluoride were applied during 60 hours). MS: m/z=211 [M]$^+$.

The starting material rac-((3aR,6aR)-5,5-difluoro-4,5,6,6a-tetrahydro-3aH-cyclopenta[d]isoxazole-3,6a-diyl)dimethanol (XLI) was obtained as follows:

To a solution of rac-((3aR,6aR)-6a-(benzyloxymethyl)-5,5-difluoro-4,5,6,6a-tetrahydro-3aH-cyclopenta[d]isoxazol-3-yl)methanol (1.52 g, 5.11 mmol) in dichloromethane (23 ml) was added dropwise at −70° C. boron trichloride (1 M in dichloromethane) (15.3 ml, 15.3 mmol). The reaction mixture was stirred at −70° C. for 1 hour, then allowed to warm to 0° C. within another hour. The reaction mixture was quenched with methanol (10 ml) at −70° C., stirred for 30 minutes at room temperature and evaporated to dryness. The residue was purified by chromatography with a 9:1-mixture of dichloromethane and methanol to give rac-((3aR,6aR)-5,5-difluoro-4,5,6,6a-tetrahydro-3aH-cyclopenta[d]isoxazole-3,6a-diyl)dimethanol (880 mg, 83% yield) as a light brown solid. MS: m/z=208.1 [M+H]$^+$.

Synthesis of the Intermediate Isoxazolidines XLIII, XLIVa and XLIVb

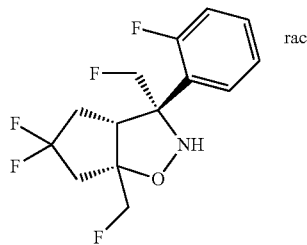

Intermediate XXXXIII was obtained following general procedure L: Starting from rac-(3aR,6aR)-5,5-difluoro-3,6a-bis(fluoromethyl)-4,5,6,6a-tetrahydro-3aH-cyclopenta[d]isoxazole (XLII), the product rac-(3S,3aR,6aR)-5,5-difluoro-3,6a-bis(fluoromethyl)-3-(2-fluorophenyl)hexahydro-2H-cyclopenta[d]isoxazole was obtained as a yellow oil. MS: m/z=308.4 [M+H]⁺.

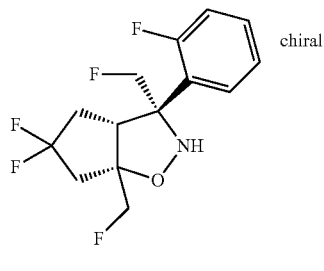

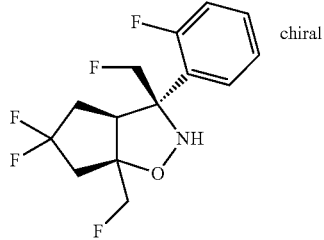

Separation of rac-(3S,3aR,6aR)-5,5-difluoro-3,6a-bis(fluoromethyl)-3-(2-fluorophenyl)hexahydro-2H-cyclopenta[d]isoxazole (XLIII) on a chiral high-performance liquid chromatography (HPLC) column (Chiralpak AD) using a 7:3-mixture of heptane and ethanol as the eluent yielded the (+)-(3S,3aR,6aR)-5,5-difluoro-3,6a-bis(fluoromethyl)-3-(2-fluorophenyl)hexahydro-2H-cyclopenta[d]isoxazole (XLIVa) as the faster eluting enantiomer and the (−)-(3R,3aS,6aS)-5,5-difluoro-3,6a-bis(fluoromethyl)-3-(2-fluorophenyl)hexahydro-2H-cyclopenta[d]isoxazole (XLIVb) as light brown solids.

Synthesis of the Intermediate Aminoalcohols XLVa and XLVb

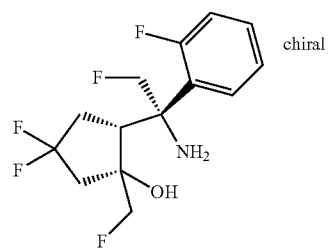

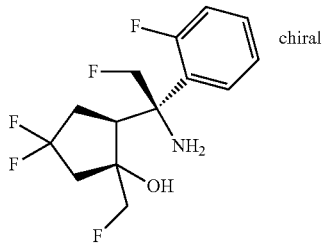

Intermediate XLVa: Following general procedure M and starting from (3S,3aR,6aR)-5,5-difluoro-3,6a-bis(fluoromethyl)-3-((2-fluorophenyl)hexahydro-2H-cyclopenta[d]isoxazole (XLIVa), the product (1R,2R)-2-((S)-1-amino-2-fluoro-1-(2-fluorophenyl)ethyl)-4,4-difluoro-1-(fluoromethyl)cyclopentanol (XLVa) was obtained as a white solid. MS: m/z=310.6 [M+H]⁺.

Intermediate XLVb: Following general procedure M and starting from (3R,3aS,6aS)-5,5-difluoro-3,6a-bis(fluoromethyl)-3-(2-fluorophenyl)hexahydro-2H-cyclopenta[d]isoxazole (XLIVb), the product (1S,2S)-2-((R)-1-amino-2-fluoro-1-(2-fluorophenyl)ethyl)-4,4-difluoro-1-(fluoromethyl)cyclopentanol (XLVb) was obtained as a white solid. MS: m/z=310.1 [M+H]⁺.

Synthesis of the Intermediate Aminooxazines XLVIa and XLVIb

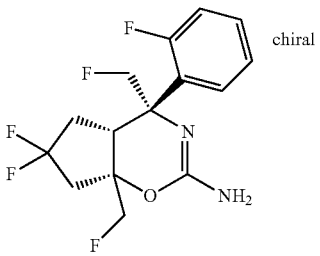

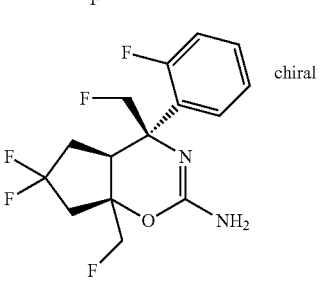

Intermediate XLVIa: Following general procedure N and starting from (1R,2R)-2-((S)-1-amino-2-fluoro-1-(2-fluorophenyl)ethyl)-4,4-difluoro-1-(fluoromethyl)cyclopentanol (XLVa), the product (4S,4aR,7aR)-6,6-difluoro-4,7a-bis(fluoromethyl)-4-(2-fluorophenyl)-4,4a,5,6,7,7a-hexahydrocyclopenta[e][1,3]oxazin-2-amine (XLVIa) was obtained as a white foam. MS: m/z=335.4 [M+H]⁺.

Intermediate XLVIb: Following general procedure N and starting from (1S,2S)-2-((R)-1-amino-2-fluoro-1-(2-fluorophenyl)ethyl)-4,4-difluoro-1-(fluoromethyl)cyclopentanol (XLVb), the product (4R,4aS,7aS)-6,6-difluoro-4,7a-bis(fluoromethyl)-4-(2-fluorophenyl)-4,4a,5,6,7,7a-hexahydrocyclopenta[e][1,3]oxazin-2-amine (XLVIb) was obtained as a white foam. MS: m/z=335.1 [M+H]⁺.

Synthesis of the Intermediate Nitro-Oxazines XLVIIa and XLVIIb

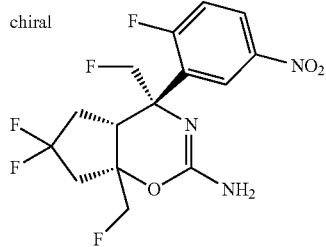

XLVIIa

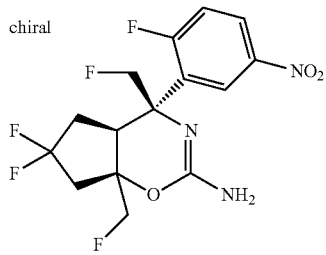

XLVIIb

Intermediate XLVIIa: Following general procedure 0 and starting from (4S,4aR,7aR)-6,6-difluoro-4,7a-bis(fluoromethyl)-4-(2-fluorophenyl)-4,4a,5,6,7,7a-hexahydrocyclopenta[e][1,3]oxazin-2-amine (XLVIa), the product (4S,4aR,7aR)-6,6-difluoro-4-(2-fluoro-5-nitrophenyl)-4,7a-bis(fluoromethyl)-4,4a,5,6,7,7a-hexahydrocyclopenta[e][1,3]oxazin-2-amine (XLVIIa) was obtained as a light brown solid. MS: m/z=380.4 [M+H]+.

Intermediate XLVIIb: Following general procedure O and starting from (4R,4aS,7aS)-6,6-difluoro-4,7a-bis(fluoromethyl)-4-(2-fluorophenyl)-4,4a,5,6,7,7a-hexahydrocyclopenta[e][1,3]oxazin-2-amine (XLVIb), the product (4R,4aS,7aS)-6,6-difluoro-4-(2-fluoro-5-nitrophenyl)-4,7a-bis(fluoromethyl)-4,4a,5,6,7,7a-hexahydrocyclopenta[e][1,3]oxazin-2-amine (XLVIIb) was obtained as a light brown solid. MS: m/z=380.4 [M+H]+.

Synthesis of the Intermediate Anilines XLVIIIa and XLVIIIb

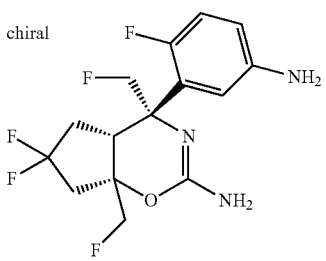

XLVIIIa

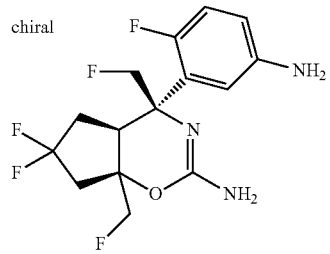

XLVIIIb

Intermediate XLVIIIa: Following general procedure P and starting from (4S,4aR,7aR)-6,6-difluoro-4-(2-fluoro-5-nitrophenyl)-4,7a-bis(fluoromethyl)-4,4a,5,6,7,7a-hexahydrocyclopenta[e][1,3]oxazin-2-amine (XLVIIa), the product (4S,4aR,7aR)-4-(5-amino-2-fluorophenyl)-6,6-difluoro-4,7a-bis(fluoromethyl)-4,4a,5,6,7,7a-hexahydrocyclopenta[e][1,3]oxazin-2-amine (XLVIIIa) was obtained as a white foam. MS: m/z=350.4 [M+H]+.

Intermediate XLVIIIb: Following general procedure P and starting from (4R,4aS,7aS)-6,6-difluoro-4-(2-fluoro-5-nitrophenyl)-4,7a-bis(fluoromethyl)-4,4a,5,6,7,7a-hexahydrocyclopenta[e][1,3]oxazin-2-amine (XLVIIb), the product (4R,4aS,7a5)-4-(5-amino-2-fluorophenyl)-6,6-difluoro-4,7a-bis(fluoromethyl)-4,4a,5,6,7,7a-hexahydrocyclopenta[e][1,3]oxazin-2-amine (XLVIIIb) was obtained as a white foam. MS: m/z=350.1 [M+H]+.

The following examples were prepared according to general procedure Q.

Example 1

5-Chloro-pyridine-2-carboxylic acid [3-((4S,4aR,7aR)-2-amino-6,6-difluoro-4-methyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-methyl-4,4a,5,6,7,7a-hexahydro-cyclopenta[e][1,3]oxazin-2-ylamine and 5-chloro-pyridine-2-carboxylic acid following procedure Q yielded the title compound as a white solid. MS: m/z=439.2 [M+H]+.

Example 2

5-Cyano-pyridine-2-carboxylic acid [3-((4S,4aR,7aR)-2-amino-6,6-difluoro-4-methyl 4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-methyl-4,4a,5,6,7,7a-hexahydro-cyclopenta[e][1,3]oxazin-2-ylamine and 5-cyano-pyridine-2-carboxylic acid following procedure Q yielded the title compound as a white solid. MS: m/z=430.3[M+H]+.

Example 3

5-Cyano-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-Amino-2-fluoro-phenyl)-6,6-difluoro-4-fluoromethyl-4,4a,5,6,7,7a-hexahydrocyclopenta[e][1,3]oxazin-2-ylamine and 5-cyano-pyridine-2-carboxylic acid following procedure Q yielded the title compound as a white solid. MS: m/z=448.1 [M+H]$^+$.

Example 4

5-Chloro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-Amino-2-fluoro-phenyl)-6,6-difluoro-4-fluoromethyl-4,4a,5,6,7,7a-hexahydro-cyclopenta[e][1,3]oxazin-2-ylamine and 5-chloro-pyridine-2-carboxylic acid following procedure Q yielded the title compound as a white solid. MS: m/z=457.1[M+H]$^+$.

Example 5

5-But-2-ynyloxy-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-Amino-2-fluoro-phenyl)-6,6-difluoro-4-fluoromethyl-4,4a,5,6,7,7a-hexahydro-cyclopenta[e][1,3]oxazin-2-ylamine and 5-but-2-ynyloxy-pyridine-2-carboxylic acid following procedure Q yielded the title compound as a white solid. MS: m/z=491.0 [M+H]$^+$.

Example 6

3,5-Dichloro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-Amino-2-fluoro-phenyl)-6,6-difluoro-4-fluoromethyl-4,4a,5,6,7,7a-hexahydro-cyclopenta[e][1,3]oxazin-2-ylamine and 3,5-dichloro-pyridine-2-carboxylic acid following procedure Q yielded the title compound as a white solid. MS: m/z=491.0 [M+H]$^+$.

Example 7

5-Fluoro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 5-fluoro-pyridine-2-carboxylic acid following procedure Q yielded the title compound as a white solid. MS: m/z=441.0 [M+H]$^+$.

Example 8

3,5-Difluoro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 3,5-difluoro-pyridine-2-carboxylic acid following procedure Q yielded the title compound as a white solid. MS: m/z=459.2 [M+H]$^+$.

Example 9

5-(2,2,2-Trifluoro-ethoxy)-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 5-(2,2,2-trifluoro-ethoxy)-pyridine-2-carboxylic acid [CAS 881409-53-6] following procedure Q yielded the title compound as an off-white foam. MS: m/z=521.2 [M+H]$^+$.

Example 10

5-(2,2,3,3,3-Pentafluoro-propoxy)-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 5-(2,2,3,3,3-pentafluoro-propoxy)-pyridine-2-carboxylic acid [CAS 1310350-87-8] following procedure Q yielded the title compound as a white foam. MS: m/z=571.2 [M+H]$^+$.

Example 11

5-(2,2,3,3-Tetrafluoro-propoxy)-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 5-(2,2,3,3-tetrafluoro-propoxy)-pyridine-2-carboxylic acid [CAS 1310350-76-5] following procedure Q yielded the title compound as a white foam. MS: m/z=553.2 [M+H]$^+$.

Example 12

5-Cyclopropylmethoxy-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 5-cyclopropylmethoxy-pyridine-2-carboxylic acid [CAS 1266787-40-9] following procedure Q yielded the title compound as a white foam. MS: m/z=493.1 [M+H]$^+$.

Example 13

5-Difluoromethoxy-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydrocyclopenta[e][1,3]oxazin-2-ylamine and 5-difluoromethoxy-pyridine-2-carboxylic acid [CAS 1174323-34-2] following procedure Q yielded the title compound as a white foam. MS: m/z=489.0 [M+H]⁺.

Example 14

5-(2,2-Difluoro-ethoxy)-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 5-(2,2-difluoro-ethoxy)-pyridine-2-carboxylic acid [CAS 1097730-45-4] following procedure Q yielded the title compound as a white solid. MS: m/z=503.1 [M+H]⁺.

Example 15

5-Trifluoromethyl-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 5-trifluoromethyl-pyridine-2-carboxylic acid [CAS 80194-69-0] following procedure Q yielded the title compound as a white solid. MS: m/z=491.0 [M+H]⁺.

Example 16

3-Chloro-5-trifluoromethyl-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 3-chloro-5-trifluoromethyl-pyridine-2-carboxylic acid [CAS 80194-68-9] following procedure Q yielded the title compound as a white solid. MS: m/z=525.1 [M+H]⁺.

Example 17

3-Fluoro-5-trifluoromethyl-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 3-fluoro-5-trifluoromethyl-pyridine-2-carboxylic acid [CAS 89402-28-8] following procedure Q yielded the title compound as a white solid. MS: m/z=509.2 [M+H]⁺.

Example 18

3-Fluoro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 3-fluoro-pyridine-2-carboxylic acid following procedure Q yielded the title compound as a white solid. MS: m/z=441.1 [M+H]⁺.

Example 19

3-Chloro-5-cyano-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 3-chloro-5-cyano-pyridine-2-carboxylic acid [CAS 1200497-81-9] following procedure Q yielded the title compound as a yellow solid. MS: m/z=482.4 [M+H]⁺, 484.4 [M+2+H]⁺.

Example 20

5-Cyano-3-fluoro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 5-cyano-3-fluoro-pyridine-2-carboxylic acid [CAS 1200498-46-9] following procedure Q yielded the title compound as a light yellow solid. MS: m/z=466.1 [M+H]⁺.

Example 21

5-Difluoromethoxy-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 5-difluoromethoxy-pyrazine-2-carboxylic acid [CAS 1174320-98-9] following procedure Q yielded the title compound as a light yellow solid. MS: m/z=490.1 [M+H]⁺.

Example 22

5-(2,2,2-Trifluoro-ethoxy)-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 5-(2,2,2-trifluoro-ethoxy)-pyrazine-2-carboxylic acid [CAS 1174323-36-4]

following procedure Q yielded the title compound as an off-white foam. MS: m/z=522.0 [M+H]+.

Example 23

5-(2,2-Difluoro-ethoxy)-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 5-(2,2-difluoro-ethoxy)-pyrazine-2-carboxylic acid [CAS 1174323-38-6] following procedure Q yielded the title compound as a white foam. MS: m/z=504.3 [M+H]+.

Example 24

5-Difluoromethyl-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 5-difluoromethyl-pyrazine-2-carboxylic acid [CAS 1174321-06-2] following procedure Q yielded the title compound as an off-white foam. MS: m/z=474.3 [M+H]+.

Example 25

5-Cyclopropylmethoxy-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 5-cyclopropyl-methoxy-pyrazine-2-carboxylic acid [CAS 1286777-19-2] following procedure Q yielded the title compound as a yellow solid. MS: m/z=494.1 [M+H]+.

Example 26

5-Fluoromethoxy-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 5-fluoromethoxy-pyrazine-2-carboxylic acid [CAS 1174321-00-6] following procedure Q yielded the title compound as a white solid. MS: m/z=472.1 [M+H]+.

Example 27

5-Chloro-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 5-chloro-pyrazine-2-carboxylic acid following procedure Q yielded the title compound as a white solid. MS: m/z=458.1 [M+H]+.

Example 28

5-Trifluoromethyl-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 5-trifluoromethyl-pyrazine-2-carboxylic acid [CAS 1060814-50-7] following procedure Q yielded the title compound as a white solid. MS: m/z=492.1 [M+H]+.

Example 29

5-(1,1-Difluoro-ethyl)-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 5-(1,1-difluoro-ethyl)-pyrazine-2-carboxylic acid [CAS 1262803-63-3] following procedure Q yielded the title compound as a white solid. MS: m/z=488.0 [M+H]+.

Example 30

5-Methoxy-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 5-methoxy-pyrazine-2-carboxylic acid [CAS 40155-42-8] following procedure Q yielded the title compound as a white foam. MS: m/z=454.4 [M+H]+.

Example 31

5-Trifluoromethyl-pyrimidine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 5-trifluoromethyl-pyrimidine-2-carboxylic acid [CAS 944905-44-6] following procedure Q yielded the title compound as a white solid. MS: m/z=492.1 [M+H]+.

Example 32

5-Chloro-pyrimidine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydrocyclopenta[e][1,3]oxazin-2-ylamine and 5-chloro-pyrimidine-2-carboxylic acid [CAS 38275-61-5] following procedure Q yielded the title compound as a white solid. MS: m/z=458.2 [M+H]$^+$.

Example 33

2-Methyl-oxazole-4-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 2-methyl-oxazole-4-carboxylic acid [CAS 23012-17-1] following procedure Q yielded the title compound as a white solid. MS: m/z=427.0 [M+H]$^+$.

Example 34

1-Methyl-1H-pyrazole-3-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 1-methyl-1H-pyrazole-3-carboxylic acid [CAS 25016-20-0] following procedure Q yielded the title compound as a white solid. MS: m/z=426.1 [M+H]$^+$.

Example 35

4-Chloro-1-difluoromethyl-1H-pyrazole-3-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluoro-phenyl)-6,6-difluoro-4-fluoromethyl-4,4a,5,6,7,7a-hexahydro-cyclopenta[e][1,3]oxazin-2-ylamine and 4-chloro-1-difluoromethyl-1H-pyrazole-3-carboxylic acid [CAS 1310350-99-2] following procedure Q yielded the title compound as a white foam. MS: m/z=496.3 [M+H]$^+$.

Example 36

5-Cyano-pyridine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluorophenyl)-4-(difluoromethyl)-6,6-difluoro-4,4a,5,6,7,7a-hexahydrocyclopenta[e][1,3]oxazin-2-ylamine (intermediate XXXIV) and 5-cyano-pyridine-2-carboxylic acid following procedure Q yielded the title compound as a white solid. MS: m/z=466.3 [M+H]$^+$.

Example 37

5-Chloro-pyridine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluorophenyl)-4-(difluoromethyl)-6,6-difluoro-4,4a,5,6,7,7a-hexahydrocyclopenta[e][1,3]oxazin-2-ylamine and 5-chloro-pyridine-2-carboxylic acid following procedure Q yielded the title compound as a white solid. MS: m/z=475.2 [M+H]$^+$.

Example 38

5-Fluoromethoxy-pyrazine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluorophenyl)-4-(difluoromethyl)-6,6-difluoro-4,4a,5,6,7,7a-hexahydrocyclopenta[e][1,3]oxazin-2-ylamine and 5-fluoromethoxy-pyrazine-2-carboxylic acid following procedure Q yielded the title compound as a white solid. MS: m/z=490.4 [M+H]$^+$.

Example 39

5-Chloro-pyrazine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluorophenyl)-4-(difluoromethyl)-6,6-difluoro-4,4a,5,6,7,7a-hexahydrocyclopenta[e][1,3]oxazin-2-ylamine and 5-chloro-pyrazine-2-carboxylic acid following procedure Q yielded the title compound as a light brown solid. MS: m/z=476.3 [M+H]$^+$.

Example 40

5-Difluoromethyl-pyrazine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluorophenyl)-4-(difluoromethyl)-6,6-difluoro-4,4a,5,6,7,7a-hexahydrocyclopenta[e][1,3]oxazin-2-ylamine and 5-difluoromethyl-pyrazine-2-carboxylic acid following procedure Q yielded the title compound as a white solid. MS: m/z=492.4 [M+H]$^+$.

Example 41

5-Difluoromethoxy-pyrazine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluorophenyl)-4-(difluoromethyl)-6,6-difluoro-4,4a,5,6,7,7a-hexahydrocyclopenta[e][1,3]oxazin-2-ylamine and 5-difluoromethoxy-pyrazine-2-carboxylic acid following procedure Q yielded the title compound as a light yellow solid. MS: m/z=508.4 [M+H]$^+$.

Example 42

5-Methoxy-pyrazine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluorophenyl)-4-(difluoromethyl)-6,6-difluoro-4,4a,5,6,7,7a-hexahydrocyclopenta[e][1,3]oxazin-2-ylamine and 5-methoxy-pyrazine-2-carboxylic acid following procedure Q yielded the title compound as a colorless solid. MS: m/z=472.5 [M+H]$^+$.

Example 43

4-Chloro-1-difluoromethyl-1H-pyrazole-3-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluorophenyl)-4-(difluoromethyl)-6,6-difluoro-4,4a,5,6,7,7a-hexahydrocyclopenta[e][1,3]oxazin-2-ylamine and 4-chloro-1-difluoromethyl-1H-pyrazole-3-carboxylic acid following procedure Q yielded the title compound as an off-white solid. MS: m/z=514.3 [M+H]$^+$.

Example 44

2-Methyl-oxazole-4-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluorophenyl)-4-(difluoromethyl)-6,6-difluoro-4,4a,5,6,7,7a-hexahydrocyclopenta[e][1,3]oxazin-2-ylamine and 2-methyl-oxazole-4-carboxylic acid following procedure Q yielded the title compound as a white solid. MS: m/z=445.4 [M+H]$^+$.

Example 45

5-Cyano-pyridine-2-carboxylic acid [3-((1S,7aS)-2-(R)-amino-6,6-difluoro-4,7a-bis-fluoromethyl-4,4a,5,6,7,7a-hexahydro-cyclopenta[e][1,3]oxazin-4-yl)-4-fluoro-phenyl]-amide The coupling of (4R,4aS,7a5)-4-(5-amino-2-fluorophenyl)-6,6-difluoro-4,7a-bis(fluoromethyl)-4,4a,5,6,7,7a-hexahydrocyclopenta[e][1,3]oxazin-2-ylamine and 5-cyano-pyridine-2-carboxylic acid following procedure Q yielded the title compound as a white solid. MS: m/z=480.5 [M+H]$^+$.

Example 46

5-Cyano-pyridine-2-carboxylic acid [3-((1R,7aR)-2-(S)-amino-6,6-difluoro-4,7a-bis-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluorophenyl)-6,6-difluoro-4,7a-bis(fluoromethyl)-4,4a,5,6,7,7a-hexahydrocyclopenta[e][1,3]oxazin-2-ylamine and 5-cyano-pyridine-2-carboxylic acid following procedure Q yielded the title compound as a white foam. MS: m/z=480.3 [M+H]$^+$.

Example 47

5-Chloro-pyridine-2-carboxylic acid [3-((1R,7aR)-2-(S)-amino-6,6-difluoro-4,7a-bis-fluoromethyl-4,4a,5,6,7,7a-hexahydro-cyclopenta[e][1,3]oxazin-4-yl)-4-fluoro-phenyl]-amide The coupling of (4S,4aR,7aR)-4-(5-amino-2-fluorophenyl)-6,6-difluoro-4,7a-bis(fluoromethyl)-4,4a,5,6,7,7a-hexahydrocyclopenta[e][1,3]oxazin-2-ylamine and 5-chloro-pyridine-2-carboxylic acid following procedure Q yielded the title compound as a white foam. MS: m/z=489.3 [M+H]$^+$, 491.3 [M+2H]$^+$.

The invention claimed is:
1. A compound of formula I,

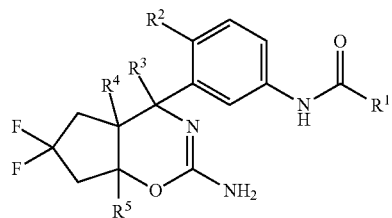

wherein
R$^1$ is selected from the group consisting of
  i) aryl,
  ii) aryl substituted by 1-4 substituents individually selected from cyano, cyano-C$_{1-6}$-alkyl, halogen, halogen-C$_{1-6}$-alkoxy, halogen-C$_{1-6}$-alkyl, C$_{1-6}$-alkoxy, C$_{1-6}$-alkoxy-C$_{1-6}$-alkyl, C$_{2-6}$-alkynyl-C$_{1-6}$-alkoxy, C$_{2-6}$-alkynyl and C$_{1-6}$-alkyl,
  iii) heteroaryl, and
  iv) heteroaryl substituted by 1-4 substituents individually selected from C$_{3-6}$-cycloalkyl-C$_{1-6}$-alkoxy, C$_{3-6}$-cycloalkyl-C$_{1-6}$-alkyl, cyano, cyano-C$_{1-6}$-alkyl, halogen, halogen-C$_{1-6}$-alkoxy, halogen-C$_{1-6}$-alkyl, C$_{1-6}$-alkoxy, C$_{1-6}$-alkoxy-C$_{1-6}$-alkyl, C$_{2-6}$-alkynyl-C$_{1-6}$-alkoxy, C$_{2-6}$-alkynyl and C$_{1-6}$-alkyl;
R$^2$ is selected from the group consisting of
  i) hydrogen,
  ii) C$_{1-6}$-alkyl, and
  iii) halogen;
R$^3$ is selected from the group consisting of
  i) C$_{1-6}$-alkyl and
  ii) halogen-C$_{1-6}$-alkyl;
R$^4$ is selected from the group consisting of
  i) hydrogen and
  ii) C$_{1-6}$-alkyl; and
R$^5$ is selected from the group consisting of
  i) hydrogen,
  ii) C$_{1-6}$-alkyl and
  iii) halogen-C$_{1-6}$-alkyl;
or a pharmaceutically acceptable salt thereof.
2. The compound of claim 1, wherein
R$^1$ is heteroaryl substituted by 1-2 substituents individually selected from C$_{3-6}$-cycloalkyl-C$_{1-6}$-alkoxy, cyano, halogen, halogen-C$_{1-6}$-alkoxy, halogen-C$_{1-6}$-alkyl, C$_{1-6}$-alkoxy, C$_{2-6}$-alkynyl-C$_{1-6}$-alkoxy and C$_{1-6}$-alkyl;
R$^2$ is halogen;
R$^3$ is selected from the group consisting of
  C$_{1-6}$-alkyl and
  halogen-C$_{1-6}$-alkyl;
R$^4$ is hydrogen; and
R$^5$ is selected from the group consisting of
  i) hydrogen and
  ii) halogen-C$_{1-6}$-alkyl;
or a pharmaceutically acceptable salt thereof.

3. The compound of claim 1, wherein
R¹ is selected from the group consisting of
  i) aryl,
  ii) aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl,
  iii) heteroaryl, and
  iv) heteroaryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl;
R² is selected from the group consisting of
  i) hydrogen,
  ii) $C_{1-6}$-alkyl, and
  iii) halogen;
R³ is selected from the group consisting of
  i) $C_{1-6}$-alkyl and
  ii) halogen-$C_{1-6}$-alkyl;
R⁴ is selected from the group consisting of
  i) hydrogen and
  ii) $C_{1-6}$-alkyl, and
R⁵ is selected from the group consisting of
  i) hydrogen and
  ii) $C_{1-6}$-alkyl;
or pharmaceutically acceptable salts thereof.

4. The compound of claim 1, wherein R¹ is heteroaryl substituted by 1-2 substituents individually selected from $C_{3-6}$-cycloalkyl-$C_{1-6}$-alkoxy, cyano, halogen, halogen-$C_{1-6}$-alkoxy, halogen-$C_{1-6}$-alkyl, $C_{1-6}$-alkoxy, $C_{2-6}$-alkynyl-$C_{1-6}$-alkoxy and $C_{1-6}$-alkyl.

5. The compound of claim 4, wherein R¹ is pyridinyl, pyrazinyl, pyrimidinyl, oxazolyl or 1H-pyrazolyl, each substituted by 1-2 substituents individually selected from $C_{3-6}$-cycloalkyl-$C_{1-6}$-alkoxy, cyano, halogen, halogen-$C_{1-6}$-alkoxy, halogen-$C_{1-6}$-alkyl, $C_{1-6}$-alkoxy, $C_{2-6}$-alkynyl-$C_{1-6}$-alkoxy and $C_{1-6}$-alkyl.

6. The compound of claim 5, wherein R¹ is pyridinyl substituted by 1-2 substituents individually selected from $C_{3-6}$-cycloalkyl-$C_{1-6}$-alkoxy, halogen-$C_{1-6}$-alkyl, cyano, halogen, halogen-$C_{1-6}$-alkoxy and $C_{2-6}$-alkynyl-$C_{1-6}$-alkoxy.

7. The compound of claim 5, wherein R¹ isoxazolyl substituted by 1-2 $C_{1-6}$-alkyl.

8. The compound of claim 5, wherein R¹ is pyrazinyl substituted by 1-2 substituents individually selected from halogen, $C_{1-6}$-alkoxy, $C_{3-6}$-cycloalkyl-$C_{1-6}$-alkoxy, halogen-$C_{1-6}$-alkoxy and halogen-$C_{1-6}$-alkyl.

9. The compound of claim 5, wherein R¹ is 1H-pyrazolyl substituted by 1-2 substituents individually selected from halogen, halogen-$C_{1-6}$-alkyl and $C_{1-6}$-alkyl.

10. The compound of claim 5, wherein R¹ is pyrimidinyl substituted by 1-2 substituents individually selected from halogen and halogen-$C_{1-6}$-alkyl.

11. The compound of claim 1, wherein R² is halogen.

12. The compound of claim 11, wherein R² is F.

13. The compound of claim 1, wherein R³ is methyl, —CHF₂ or —CH₂F.

14. The compound of claim 1, wherein R⁴ is hydrogen.

15. The compound of claim 1, wherein R⁵ is hydrogen.

16. The compound of claim 1, wherein R⁵ is —CH₂F.

17. The compound of claim 1, selected from the group consisting of

5-But-2-ynyloxy-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Cyclopropylmethoxy-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Difluoromethoxy-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Trifluoromethyl-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 3-Chloro-5-trifluoromethyl-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 3-Fluoro-5-trifluoromethyl-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 3-Chloro-5-cyano-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Cyano-3-fluoro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Difluoromethoxy-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, and 5-Difluoromethyl-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide or a pharmaceutically acceptable salt thereof.

18. The compound of claim 1, selected from the group consisting of

5-Cyclopropylmethoxy-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Fluoromethoxy-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Trifluoromethyl-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Trifluoromethyl-pyrimidine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, Methyl-1H-pyrazole-3-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 4-Chloro-1-difluoromethyl-1H-pyrazole-3-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Cyano-pyridine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide, 5-Chloro-pyridine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide, 5-Fluoromethoxy-pyrazine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide, and 5-Chloro-pyrazine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide or a pharmaceutically acceptable salt thereof.

19. The compound of claim 1, selected from the group consisting of

5-Difluoromethyl-pyrazine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide, 5-Difluoromethoxy-pyrazine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide, 5-Methoxy-pyrazine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide, 4-Chloro-1-difluoromethyl-1H-pyrazole-3-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide, 2-Methyl-oxazole-4-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide, 5-(2,2,2-Trifluoro-ethoxy)-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-(2,2,2-Trifluoro-ethoxy)-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-(2,2,3,3-Tetrafluoro-propoxy)-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-(2,2,3,3,3-Pentafluoro-propoxy)-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, and 5-Chloro-pyridine-2-carboxylic acid [3-((4S,4aR,7aR)-2-amino-6,6-difluoro-4-methyl-4,4a,5,6,7,7a-hexahydro-cyclopenta[e][1,3]oxazin-4-yl)-4-fluoro-phenyl]-amide or a pharmaceutically acceptable salt thereof.

20. The compound of claim 1, selected from the group consisting of

5-Cyano-pyridine-2-carboxylic acid [3-((4S,4aR,7aR)-2-amino-6,6-difluoro-4-methyl 4,4a,5,6,7,7a-hexahydro-cyclopenta[e][1,3]oxazin-4-yl)-4-fluoro-phenyl]-amide, 5-Cyano-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Chloro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Fluoro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 3-Fluoro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Chloro-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Methoxy-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Chloro-pyrimidine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 2-Methyl-oxazole-4-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, and 5-Cyano-pyridine-2-carboxylic acid [3-((1S,7aS)-2-(R)-amino-6,6-difluoro-4,7a-bis-fluoromethyl-4,4a,5,6,7,7a-hexahydro-cyclopenta[e][1,3]oxazin-4-yl)-4-fluoro-phenyl]-amide or a pharmaceutically acceptable salt thereof.

21. The compound of claim 1, selected from the group consisting of

5-Cyano-pyridine-2-carboxylic acid [3-((1R,7aR)-2-(S)-amino-6,6-difluoro-4,7a-bis-fluoromethyl-4,4a,5,6,7,7a-hexahydro-cyclopenta[e][1,3]oxazin-4-yl)-4-fluoro-phenyl]-amide, 5-Chloro-pyridine-2-carboxylic acid [3-((1R,7aR)-2-(S)-amino-6,6-difluoro-4,7a-bis-fluoromethyl-4,4a,5,6,7,7a-hexahydro-cyclopenta[e][1,3]oxazin-4-yl)-4-fluoro-phenyl]-amide, 5-(1,1-Difluoro-ethyl)-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-(2,2-Difluoro-ethoxy)-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-(2,2-Difluoro-ethoxy)-pyrazine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 3,5-Dichloro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, and 3,5-Difluoro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, or a pharmaceutical acceptable salt thereof.

22. The compound of claim 1, selected from the group consisting of

5-Chloro-pyridine-2-carboxylic acid [3-((4S,4aR,7aR)-2-amino-6,6-difluoro-4-methyl-4,4a,5,6,7,7a-hexahydro-cyclopenta[e][1,3]oxazin-4-yl)-4-fluoro-phenyl]-amide, 5-Cyano-pyridine-2-carboxylic acid [3-((4S,4aR,7aR)-2-amino-6,6-difluoro-4-methyl 4,4a,5,6,7,7a-hexahydro-cyclopenta[e][1,3]oxazin-4-yl)-4-fluoro-phenyl]-amide, 5-Cyano-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-Chloro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 5-But-2-ynyloxy-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, 3,5-Dichloro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, and 5-Fluoro-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide, or a pharmaceutical acceptable salt thereof.

23. The compound of claim 1, selected from the group consisting of

5-Chloro-pyridine-2-carboxylic acid [3-((4S,4aR,7aR)-2-amino-6,6-difluoro-4-methyl-4,4a,5,6,7,7a-hexahydro-cyclopenta[e][1,3]oxazin-4-yl)-4-fluoro-phenyl]-amide, and 5-Cyano-pyridine-2-carboxylic acid [(S)-3-((1R,2R)-2-amino-6,6-difluoro-4-fluoromethyl-4,4a,5,6,7,7a-hexahydro-cyclopenta[e][1,3]oxazin-4-yl)-4-fluoro-phenyl]-amide.

24. The compound of claim 1, which is 5-Methoxy-pyrazine-2-carboxylic acid [(S)-3-((1R,2R)-2-amino-4-difluoromethyl-6,6-difluoro-4,4a,5,6,7,7a-hexahydro-cyclopenta[e][1,3]oxazin-4-yl)-4-fluoro-phenyl]-amide.

25. A pharmaceutical composition comprising a therapeutically effective amount of a compound of formula I

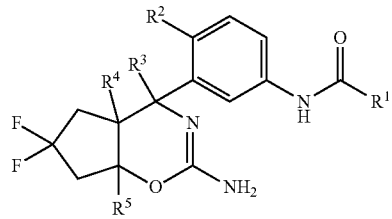

wherein $R^1$ is selected from the group consisting of
i) aryl,
ii) aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl,
iii) heteroaryl, and
iv) heteroaryl substituted by 1-4 substituents individually selected from $C_{3-6}$-cycloalkyl-$C_{1-6}$-alkoxy, $C_{3-6}$-cycloalkyl-$C_{1-6}$-alkyl, cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl;

$R^2$ is selected from the group consisting of
i) hydrogen,
ii) $C_{1-6}$-alkyl, and
iii) halogen;

$R^3$ is selected from the group consisting of
i) $C_{1-6}$-alkyl and
ii) halogen-$C_{1-6}$-alkyl;

$R^4$ is selected from the group consisting of
i) hydrogen and
ii) $C_{1-6}$-alkyl; and $R^5$ is selected from the group consisting of
i) hydrogen,
ii) $C_{1-6}$-alkyl and
iii) halogen-$C_{1-6}$-alkyl;

or a pharmaceutically acceptable salt thereof and a pharmaceutically acceptable carrier.

* * * * *